(12) United States Patent
Kimchy

(10) Patent No.: US 7,787,926 B2
(45) Date of Patent: Aug. 31, 2010

(54) INTRA-LUMEN POLYP DETECTION

(75) Inventor: Yoav Kimchy, Haifa (IL)

(73) Assignee: Check-Cap LLC, Isfiya, Mt. Carmel (IL)

( * ) Notice: Subject to any disclaimer, the term of this patent is extended or adjusted under 35 U.S.C. 154(b) by 620 days.

(21) Appl. No.: 10/596,065

(22) PCT Filed: Dec. 16, 2004

(86) PCT No.: PCT/IL2004/001140

§ 371 (c)(1),
(2), (4) Date: May 26, 2006

(87) PCT Pub. No.: WO2005/058129

PCT Pub. Date: Jun. 30, 2005

(65) Prior Publication Data

US 2007/0161885 A1    Jul. 12, 2007

Related U.S. Application Data

(60) Provisional application No. 60/531,690, filed on Dec. 17, 2003, provisional application No. 60/559,695, filed on Mar. 31, 2004.

(51) Int. Cl.
*A61B 5/05* (2006.01)
*A61B 6/00* (2006.01)
(52) U.S. Cl. .................... 600/407; 600/436
(58) Field of Classification Search ............ 600/407
See application file for complete search history.

(56) References Cited

U.S. PATENT DOCUMENTS

| | | | |
|---|---|---|---|
| 4,217,045 A | 8/1980 | Ziskind | |
| 4,689,621 A | 8/1987 | Kleinberg | |
| 4,726,381 A | 2/1988 | Jones | |
| 4,763,658 A | 8/1988 | Jones | |
| 4,765,339 A | 8/1988 | Jones | |
| 4,774,955 A | 10/1988 | Jones | |

(Continued)

FOREIGN PATENT DOCUMENTS

EP    0390478    10/1990

(Continued)

OTHER PUBLICATIONS

Caner B.E., et al., "Functional assessment of human gastrointestinal tract using 99Tcm-latex particles", Abstracat Only, Nucl. Med. Commun., 12(6):539-544 (1991).

(Continued)

*Primary Examiner*—Long V Le
*Assistant Examiner*—Hien Nguyen
(74) *Attorney, Agent, or Firm*—Rissman Hendircks & Oliverio, LLP

(57) ABSTRACT

Apparatus (40) is provided, including a capsule (50), adapted to be swallowed by a subject (54), the capsule (50) including (a) at least one radiation source (60), adapted to emit radiation having an energy of at least 10 keV, and (b) at least one photon detector (62), adapted to detect photons generated responsively to the emitted radiation, the photons having an energy of at least 10 keV. The apparatus (40) additionally includes a control unit (64), adapted to analyze data regarding the photons in order to generate information useful for identifying a clinically-relevant feature of a gastrointestinal (GI) tract (72) of the subject (54).

29 Claims, 21 Drawing Sheets

U.S. PATENT DOCUMENTS

| | | | |
|---|---|---|---|
| 4,803,992 A | 2/1989 | Lemelson | |
| 4,844,076 A | 7/1989 | Lesho et al. | |
| 4,883,063 A | 11/1989 | Bernard et al. | |
| 5,003,980 A | 4/1991 | Loo et al. | |
| 5,353,807 A | 10/1994 | DeMarco | |
| 5,372,133 A | 12/1994 | Hogen Esch | |
| 5,395,366 A * | 3/1995 | D'Andrea et al. | 604/890.1 |
| 5,415,181 A | 5/1995 | Hogrefe et al. | |
| 5,422,926 A | 6/1995 | Smith et al. | |
| 5,604,531 A | 2/1997 | Iddan et al. | |
| 5,721,462 A | 2/1998 | Shanks | |
| 5,778,882 A | 7/1998 | Raymond et al. | |
| 5,792,053 A | 8/1998 | Skladnev et al. | |
| 5,800,350 A | 9/1998 | Coppleson et al. | |
| 5,829,437 A | 11/1998 | Bridges | |
| 5,833,603 A | 11/1998 | Kovacs et al. | |
| 5,842,977 A | 12/1998 | Lesho et al. | |
| 5,853,005 A | 12/1998 | Scanlon | |
| 5,993,378 A | 11/1999 | Lemelson | |
| 6,134,300 A | 10/2000 | Trebes et al. | |
| 6,169,914 B1 | 1/2001 | Hovland et al. | |
| 6,173,201 B1 | 1/2001 | Front | |
| 6,240,312 B1 | 5/2001 | Alfano et al. | |
| 6,254,548 B1 | 7/2001 | Ishikawa et al. | |
| 6,317,927 B1 | 11/2001 | Lai et al. | |
| 6,324,418 B1 | 11/2001 | Crowley et al. | |
| 6,343,227 B1 | 1/2002 | Crowley | |
| 6,353,658 B1 | 3/2002 | Trebes et al. | |
| 6,368,275 B1 | 4/2002 | Sliwa et al. | |
| 6,368,331 B1 | 4/2002 | Front et al. | |
| 6,400,974 B1 | 6/2002 | Lesho | |
| 6,423,056 B1 | 7/2002 | Ishikawa et al. | |
| 6,428,531 B1 | 8/2002 | Visuri et al. | |
| 6,428,569 B1 | 8/2002 | Brown | |
| 6,440,069 B1 | 8/2002 | Raymond et al. | |
| 6,453,199 B1 * | 9/2002 | Kobozev | 607/40 |
| 6,567,687 B2 | 5/2003 | Front et al. | |
| 6,582,365 B1 | 6/2003 | Hines et al. | |
| 6,584,348 B2 | 6/2003 | Glukhovsky | |
| 6,607,301 B1 | 8/2003 | Glukhovsky et al. | |
| 6,629,776 B2 | 10/2003 | Bell et al. | |
| 6,632,175 B1 * | 10/2003 | Marshall | 600/309 |
| 6,709,387 B1 | 3/2004 | Glukhovsky et al. | |
| 6,719,684 B2 * | 4/2004 | Kim et al. | 600/101 |
| 6,764,440 B2 * | 7/2004 | Iddan et al. | 600/109 |
| 6,776,165 B2 | 8/2004 | Jin | |
| 2001/0038831 A1 * | 11/2001 | Park et al. | 424/78.31 |
| 2001/0041835 A1 | 11/2001 | Front et al. | |
| 2001/0051766 A1 * | 12/2001 | Gazdzinski | 600/309 |
| 2002/0026108 A1 * | 2/2002 | Colvin, Jr. | 600/316 |
| 2002/0099310 A1 | 7/2002 | Kimchy et al. | |
| 2003/0139661 A1 * | 7/2003 | Kimchy et al. | 600/407 |
| 2004/0015075 A1 | 1/2004 | Kimchy et al. | |
| 2004/0054248 A1 | 3/2004 | Kimchy et al. | |
| 2004/0054278 A1 | 3/2004 | Kimchy et al. | |
| 2004/0204646 A1 | 10/2004 | Nagler et al. | |
| 2004/0250124 A1 | 12/2004 | Chesla et al. | |
| 2005/0055174 A1 | 3/2005 | David et al. | |
| 2005/0205792 A1 | 9/2005 | Rousso et al. | |
| 2005/0266074 A1 | 12/2005 | Zilberstein et al. | |
| 2006/0033029 A1 | 2/2006 | Popper | |
| 2006/0217593 A1 | 9/2006 | Gilad et al. | |
| 2006/0237652 A1 | 10/2006 | Kimchy et al. | |
| 2007/0156047 A1 | 7/2007 | Nagler et al. | |

FOREIGN PATENT DOCUMENTS

| | | |
|---|---|---|
| WO | WO 00/49958 | 8/2000 |
| WO | WO 01/62134 | 8/2001 |
| WO | WO 02/16965 | 2/2002 |
| WO | 02058531 | 8/2002 |
| WO | WO 02/058531 | 8/2002 |
| WO | WO 2004/042546 | 5/2004 |
| WO | WO 2005/067383 | 7/2005 |
| WO | WO 2005/104939 | 11/2005 |
| WO | WO 2005/112895 | 12/2005 |

OTHER PUBLICATIONS

Gutman G. et al., "A novel needle-based miniature x-ray generating system", Abstract Only, Phys. Med. Biol., 49(20):4677-4688 (2004).

Compton, Arthur H., 1923. "A Quantum Theory of the Scattering of X-Rays by Light Elements". Physical Review 21: 483-502.

Compton, Arthur H., 1923. "The Spectrum of Scattered X-rays". Physical Review 22: 409-413.

Haga, et al., 2004. "A miniature x-ray tube". Applied Physics Letters 84: 2208-2210.

Madsen, et al., 1989. "Gastrointestinal Transit of Technetium-99m-Labeled Cellulose Fiber and Indium-111-Labeled Plastic Particles". Journal of Nuclear Medicine 30: 402-406.

Proano, et al., 1990. "Transit of solids through the human colon: regional quantification in the unprepared bowel". Am. J. Physiol. 258: G856-G862.

Tartari, et al., 2000. "Compton Scattering Elemental Imaging of a Deep Layer Performed with the Principal Component Analysis". Proc. of the 15th World Conference on Non-destructive Testing, Conservation and Restoration in Art and Architecture, Rome, Oct. 15-21, 2000.

"X-ray contrast medium". Encyclopaedia of Medical Imaging, vol. 1. www.medcyclopaedia.com.

Brochard, et al., 2003. "Estimation of movement parameters of 3D textured surfaces using the autocorrelation function". Pattern Recognition Letters 24: 2031-2045.

Camilleri, et al., 1989. "Human gastric emptying and colonic filling of solids characterized by a new method". Am. J. Physiol. 257: G284-G290.

U.S. Appl. No. 60/531,690.

U.S. Appl. No. 60/559,695.

* cited by examiner

INTRA-LUMEN POLYP DETECTION

CROSS-REFERENCE TO PRIOR APPLICATION

The above-referenced application is the U.S. National Phase of International Patent Application PCT/IL2004/001140, filed Dec. 16, 2004, which claims priority from U.S. Provisional Application No. 60/531,690, filed Dec. 17, 2003 and U.S. Provisional Application No. 60/559,695, filed Mar. 31, 2004, which are incorporated by reference herein. The International application was published on Jun. 30, 2005 as WO 2005/058129 A2.

FIELD OF THE INVENTION

The present invention relates generally to the field of detection of conditions of a body lumen, and specifically to a swallowable device that travels in the colon and detects anatomical anomalies.

BACKGROUND OF THE INVENTION

Colorectal cancer is one of the leading causes of death in the Western world. Clinical evidence suggests that early detection of primary colorectal cancer leads to a 90% or better 5-year survival rate, while detection of the disease when it has already metastasized leads to poor prognosis with a 50% or less 5-year survival rate and a 30% recurrence rate. Colorectal cancer screening and early detection have a substantial positive impact on the prognosis of this malignancy.

The following references, all of which are incorporated herein by reference, may be of interest:

U.S. Pat. No. 5,721,462 to Shanks

U.S. Pat. Nos. 6,134,300 and 6,353,658 to Trebes et al.

US Patent Application Publication 2002/0099310 to Kimchy et al.

PCT Publication WO 02/058531 to Kimchy et al.

Brochard J et al., "Estimation of movement parameters of 3D textured surfaces using the autocorrelation function," Pattern Recognition Letters 24(12):2031-2045 (2003)

Camilleri M et al., "Human gastric emptying and colonic filing of solids characterized by a new method," Am J Physiol 257(2 Pt 1):G284-G290 (1989)

Caner B E et al., "Functional assessment of human gastrointestinal tract using 99Tcm-latex particles," Nucl Med Commun 12(6):539-544 (1991)

Compton, Arthur H., Phys. Rev. 21,483; 22,409 (1923)

Gutman G et al., "A novel needle-based miniature x-ray generating system," Phys Med Biol 49:4677-4688 (2004)

Haga A et al., "A miniature x-ray tube," Applied Physics Letters 84(12):2208-2210 (2004)

Madsen J L et al., "Gastrointestinal transit of technetium-99m-labeled cellulose fiber and indium-111-labeled plastic particles," J Nucl Med 30(3):402-406 (1989)

Pais, Abraham, 'Subtle is the Lord . . . ': The Science and the Life of Albert Einstein, Oxford (1982)

Proano M et al., "Transit of solids through the human colon: regional quantification in the unprepared bowel," Am J Physiol 258(6 Pt 1):G862 (1990)

Tartari A et al., "Compton scattering elemental imaging of a deep layer performed with the principal component analysis," Proceedings of the 15th World Conference on Non-Destructive Testing, Conservation and Restoration in Art and Architecture, Rome (Oct. 15-21, 2000)

"X-ray contrast medium," Medcyclopaedia™, from The Encyclopaedia of Medical Imaging Volume I

SUMMARY OF THE INVENTION

Embodiments of the present invention are directed at the detection of polyps and other clinically-relevant features that may harbor the potential for cancer of the gastrointestinal (GI) tract, particularly colorectal cancer.

In some embodiments of the present invention, a subject swallows a contrast agent, and, typically after a waiting period, a capsule comprising one or more gamma and/or X-ray radiation sources and radiation detectors. As the capsule travels through the GI tract, the radiation sources "illuminate" the vicinity of the capsule. The GI contents (including the contrast agent), GI wall, and tissue outside of the GI tract act as a scattering media for the emitted radiation, typically primarily through the process of Compton scattering. The scattered photons then travel back through the GI contents, which include the contrast agent. The radiation detectors count appropriately Compton backscattered photons, and transmit the count rate information to an external recording unit worn by the subject.

The count rates collected by each detector per unit time interval are analyzed, typically only for predetermined photon energy windows. These data are presented to a physician in a manner that enables him to assess the likelihood that there is a polyp or some other anatomical deformation in the GI tract. In some embodiments, the data are also analyzed to indicate a general area of the colon where such a deformation may exist. These polyps or anatomical anomalies may be the result of a tumor beginning to grow within the GI tract. If the physician suspects the presence of a polyp or some other anatomical anomaly that may be cancerous or pre-cancerous, the subject is typically referred for further diagnostic testing, such as colonoscopic examination.

There is therefore provided, in accordance with an embodiment of the present invention, apparatus including:

a capsule, adapted to be swallowed by a subject, and including:

at least one radiation source, adapted to emit radiation having an energy of at least 10 keV; and at least one photon detector, adapted to detect photons generated responsively to the emitted radiation, the photons having an energy of at least 10 keV; and a control unit, adapted to analyze data regarding the photons in order to generate information useful for identifying a clinically-relevant feature of a gastrointestinal (GI) tract of the subject.

In an embodiment of the present invention, the apparatus includes an oral contrast agent, adapted to be administered to the subject. Alternatively or additionally, the apparatus includes an oral agent having a high Z, adapted to be administered to the subject.

For some applications, the apparatus includes an oral agent adapted to be administered to the subject, the agent selected from the list consisting of: a contrast agent and a high Z agent, the agent includes ferromagnetic particles, and the capsule includes a magnet, adapted to attract the ferromagnetic particles to the capsule.

In an embodiment of the present invention, the radiation source includes a miniature X-ray generator. In an embodiment, the radiation source includes a radioisotope. For some applications, the radiation source is adapted to emit gamma rays. Alternatively or additionally, the radiation source is adapted to emit X-rays.

For some applications, the control unit is adapted to analyze a time derivative of the data in order to generate the information.

For some applications, the radiation source includes at least one collimator, adapted to collimate the radiation emitted by the radiation source. For some applications, the photon detector includes at least one collimator, adapted to collimate the photons detected by the photon detector.

For some applications, the control unit is adapted to distinguish between gas in the GI tract and the clinically-relevant feature.

In an embodiment, the control unit is adapted to analyze X-ray fluorescence (XRF) photons generated responsively to the emitted radiation. In an embodiment, the control unit is adapted to analyze XRF photons generated responsively to the emitted radiation, and Compton backscattered photons generated responsively to the emitted radiation.

For some applications, the capsule includes an acceleration sensor.

For some applications, the apparatus includes an external data-recording unit, adapted to remain outside a body of the subject, and the capsule is adapted to wirelessly transmit information to the data-recording unit while the capsule is in the GI tract.

For some applications, the capsule includes an agent selected from the list consisting of: a contrast agent and a high Z agent, and the capsule is adapted to store the agent and release the agent in an area of clinical interest in the GI tract. Alternatively or additionally, the apparatus includes an agent-storage capsule including an agent selected from the list consisting of: a contrast agent and a high Z agent, the agent-storage capsule adapted to store the agent and release the agent in an area of clinical interest in the GI tract.

For some applications, the capsule includes a pressure sensor.

For some applications, the data regarding the photons include data for one or more predefined photon energy windows, and the control unit is adapted to analyze the energy window data.

In an embodiment, the data regarding the photons include a number of the photons per time interval, the photon detector is adapted to count the detected photons, and the control unit is adapted to analyze the counted number of photons.

In an embodiment, the control unit is adapted to estimate a distance from a site of the capsule to a wall of the GI tract. For some applications, the control unit is adapted to estimate the distance using an algorithm in which there is an inverse relationship between the distance and a count of the detected photons. For some applications, the control unit is adapted to analyze Compton backscattered photons generated responsively to the emitted radiation. For some applications, the apparatus includes an oral contrast agent, adapted to be administered to the subject, and the control unit is adapted to estimate the distance by estimating a depth of the contrast agent between the site of the capsule and the wall of the GI tract responsively to the analysis of the Compton backscattered photons.

For some applications, the control unit is adapted to estimate the distance using an algorithm in which there is a direct relationship between the distance and a count of the detected photons. For some applications, the control unit is adapted to analyze XRF photons generated responsively to the emitted radiation. For some applications, the apparatus includes an oral agent having a high Z, adapted to be administered to the subject, the XRF photons are generated by the oral agent responsively to the emitted radiation, and the control unit is adapted to estimate the distance by estimating a depth of the agent between the site of the capsule and the wall of the GI tract responsively to the analysis of the XRF photons.

In an embodiment, the radiation source is adapted to emit the radiation from the capsule only a portion of a time that the capsule is in the GI tract. For some applications, the capsule includes a sensor, adapted to sense a parameter indicative of possible imminent motion of the capsule in the GI tract, and the radiation source is adapted to emit the radiation from the capsule responsively to the sensing of the parameter by the sensor. For some applications, the radiation source includes a miniature X-ray generator, configured to emit the radiation only during the portion of the time.

For some applications, the radiation source includes a radioisotope, the capsule includes a radiation shield, and the capsule includes an actuator, adapted to move at least one of the radiation source and the shield, such that the shield does not block the radiation emitted from the radiation source during the portion of the time. For some applications, the capsule includes a plurality of collimators, and the collimators and the shield are configured such that, at any given time, the radiation emitted by the radiation source passes through less than all of the collimators. For some applications, the capsule includes a rod, the radiation source is coupled to the rod, and the actuator is adapted to move the rod in order to move the radiation source. For some applications, the capsule includes at least one spring, and the rod and spring are configured to form a mechanical oscillator.

In an embodiment, the capsule includes an inflatable balloon, adapted to inflate around the capsule. For some applications, the balloon is configured such that the capsule moves towards a center of the balloon upon inflation thereof. For some applications, the balloon is configured to inflate when the capsule reaches an area of clinical interest within the GI tract. For some applications, the balloon includes a valve, adapted to open a certain period of time after the capsule reaches the area of clinical interest, thereby allowing the balloon to deflate.

For some applications, the control unit is adapted to estimate a wall distance from a capsule site of the capsule to a wall of the GI tract by calculating a sum of (a) a first distance within the balloon from the capsule site to a balloon site on a surface of the balloon and (b) a second distance from the balloon site to the wall of the GI tract. For some applications, the control unit is adapted to calculate the first distance by measuring and analyzing changes in Compton backscattered photon counts detected by the photon detector. For some applications, the control unit is adapted to calculate the first distance responsively to a size of a Compton backscattering projection detected by the photon detector. For some applications, the surface of the balloon includes point particles including a high density material, and the control unit is adapted to calculate the first distance by measuring and analyzing XRF photon counts detected by the photon detector. For some applications, the surface of the balloon includes radiation point sources, and the control unit is adapted to calculate the first distance by measuring and analyzing radiation emitted from the point sources and detected by the photon detector. For some applications, the control unit is adapted to calculate the second distance by analyzing XRF photon counts detected by the photon detector.

In an embodiment, the GI tract includes a colon of the subject, and the control unit is adapted to analyze the data in order to generate the information useful for identifying the clinically-relevant feature of the colon. For some applications, the capsule includes: electrodes coupled to an external surface of the capsule; and a pulse generator, and the control unit is adapted to drive the pulse generator to apply an electrical signal to the colon capable of inducing a mass movement in the colon. For some applications, the control unit is adapted to generate the information regarding a geometry of muscles of the colon.

In an embodiment, the control unit is adapted to generate a graphical representation of the information. For some applications, the control unit is adapted to generate the graphical representation by generating a series of morphologies in time. For some applications, the control unit is adapted to generate the graphical representation by generating a first surface having subdivisions representing respective distances between respective sites of the capsule and respective sites of a wall of the GI tract, and generating a second surface having pixels, each of which pixels represents a respective difference between one of the subdivisions of the first surface and a plurality of subdivisions neighboring the one of the subdivisions. For some applications, the control unit is adapted to generate the graphical representation by repeatedly generating the second surface at a plurality of points in time, and displaying an animation of the second surface corresponding to the plurality of points in time.

For some applications, the control unit is adapted to generate the graphical representation with reference to a coordinate system of the subject. Alternatively, the control unit is adapted to generate the graphical representation with reference to a coordinate system of the capsule.

In an embodiment, the at least one photon detector includes a plurality of photon detectors, arranged to detect photons arriving from a plurality of respective detection directions. For some applications, the at least one radiation source includes a plurality of collimators, arranged to emit the radiation in a plurality of respective emission directions corresponding to the detection directions.

In an embodiment, the capsule includes at least one radiation shield. For some applications, the at least one shield is configured to prevent radiation from being emitted from the radiation source in directions other than a single confined solid sector relative to a sphere surrounding the capsule.

In an embodiment, the radiation source is adapted to emit radiation having a primary plurality of energy levels, and the control unit is adapted to analyze counts of photons having a secondary plurality of energy levels, different from the primary plurality of energy levels. For some applications, the radiation source is adapted to emit radiation having first and second energy levels, and the control unit is adapted to analyze a mathematical relationship between (a) a count of the photons detected by the photon detector having a third energy level and (b) a count of the photons detected by the photon detector having a fourth energy level. For some applications, the relationship includes a ratio of (a) the count of the photons having the third energy level to (b) the count of the photons having the fourth energy level, and the control unit is adapted to analyze the ratio. For some applications, the control unit is adapted to analyze the relationship to determine an actual, calibrated distance between a site of the capsule and a wall of the GI tract.

In an embodiment, the clinically-relevant feature includes a pathological abnormality of the GI tract. In an embodiment, the pathological abnormality includes a polyp.

In an embodiment, the control unit is adapted to analyze Compton backscattered photons generated responsively to the emitted radiation. For some applications, the control unit is adapted to analyze Compton backscattered photons having an energy level indicative of a backscattering angle of 180 degrees +/− a range parameter that is less than 30 degrees, e.g., less than 20 degrees, or less than 10 degrees.

In an embodiment, the control unit is adapted to detect that the capsule has reached an area of clinical interest within the GI tract. In an embodiment, the area includes the colon, and the control unit is adapted to detect that the capsule has reached the colon. For some applications, the control unit is adapted to detect that the capsule has reached the area by detecting and analyzing XRF photons. Alternatively or additionally, the capsule includes a pH-sensitive element, and the control unit is adapted to detect that the capsule has reached the area responsively to change in pH in the area that affects the pH-sensitive element. Further alternatively or additionally, the apparatus includes a tag adapted to be coupled to an external surface of a body of the subject in a vicinity of an entrance to the area, and the control unit is adapted to detect that the capsule has reached the area responsively to a signal emitted by the tag. Still further alternatively or additionally, the capsule includes a pressure sensor, and the control unit is adapted to detect that the capsule has reached the area responsively to a change in pressure detected by the pressure sensor. For some applications, the apparatus includes a tag adapted to be coupled to an external surface of a body of the subject in a vicinity of an entrance to the area, and the control unit is adapted to detect that the capsule has reached the area responsively to (a) a signal emitted by the tag in combination with (b) the change in pressure. For some applications, the control unit is adapted to detect that the capsule has reached the area by detecting and analyzing XRF photons, and responsively to the change in pressure.

In an embodiment, the control unit is adapted to detect a variation of density in tissue of a wall of the GI tract, which variation is indicative of a presence of the clinically-relevant feature. For some applications, the control unit is adapted to detect the variation when the control unit detects that at least a portion of the capsule is in physical contact with the wall of the GI tract. For some applications, the at least one photon detector includes a plurality of photon detectors, and the control unit is adapted to analyze Compton backscattered photon counts from a site of the wall, detected by more than one of the photon detectors. For some applications, the control unit is adapted to analyze the Compton backscattered photon counts using principal component analysis (PCA). For some applications, the control unit is adapted to detect the variation of density responsively to a determination that a large fraction of a data variance cannot be described by a single principal component (PC).

In an embodiment, the capsule includes at least one extending element, adapted, when extended, to maintain the capsule at least a certain distance from a wall of the GI tract. For some applications, the extending element is configured to extend when the capsule reaches an area of clinical interest within the GI tract. For some applications, the extending element includes at least one leg-shaped element, an expandable ring structure, and/or an unfolding element.

In an embodiment, the capsule includes at least one extending element, adapted, when extended, to orient a long axis of the capsule generally parallel to a longitudinal axis of the GI tract. For some applications, the extending element includes an expandable flexible chamber. For some applications, the flexible chamber includes a super-absorbent hydrogel, and the flexible chamber is adapted to expand when the hydrogel absorbs liquids from the GI tract.

There is also provided, in accordance with an embodiment of the present invention, apparatus including:

a capsule, adapted to be swallowed by a subject, and including at least one photon detector, adapted to detect photons having a detector energy of at least 10 keV; and a control unit, adapted to analyze data regarding the photons in order to generate information useful for identifying a clinically-relevant feature of a gastrointestinal (GI) tract of the subject.

In an embodiment, the apparatus includes a radiolabeled material adapted to be swallowed by the subject and to emit radiation having a radiolabeled energy, and the control unit is adapted to analyze the data regarding the photons having the radiolabeled energy.

In an embodiment, the photon detector is collimated.

In an embodiment, the control unit is adapted to estimate a distance from a site of the capsule to a wall of the GI tract. For some applications, the control unit is adapted to estimate the distance using an algorithm in which there is a direct relationship between the distance and a count of the detected photons.

There is further provided, in accordance with an embodiment of the present invention, apparatus including:

a capsule, adapted to be swallowed by a subject, including at least one radiation source, adapted to emit radiation having an energy of at least 10 keV;

at least one photon detector not physically coupled to the capsule, adapted to detect photons having an energy of at least 10 keV; and a control unit, adapted to analyze data regarding the photons in order to generate information useful for identifying a clinically-relevant feature of a gastrointestinal (GI) tract of the subject.

In an embodiment, the radiation source includes at least one collimator, adapted to collimate the radiation emitted by the radiation source. In an embodiment, the radiation source includes a miniature X-ray generator. Alternatively, the radiation source includes a radioisotope.

There is still further provided, in accordance with an embodiment of the present invention, apparatus including:

a capsule, adapted to be swallowed by a subject, including a plurality of photon detectors;

a balloon, adapted, when inflated, to surround at least a portion of the capsule, and including at a surface thereof a plurality of radiation sources, adapted to emit radiation having an energy of at least 10 keV, wherein the photon detectors are adapted to detect photons generated responsively to the radiation, the photons having an energy of at least 10 keV; and a control unit, adapted to analyze data regarding the photons in order to generate information useful for identifying a clinically-relevant feature of a gastrointestinal (GI) tract of the subject.

In an embodiment, the control unit is adapted to analyze XRF photons detected by the photon detectors in order to estimate a distance between a site on the surface of the balloon and a wall of the GI tract.

In an embodiment, the control unit is adapted to analyze Compton backscattered photons having an energy level indicative of a backscattering angle of 180 degrees +/- a range parameter that is less than 30 degrees.

In an embodiment, the control unit is adapted to analyze incident photons having a same energy as the radiation emitted by the radiation sources. For some applications, the control unit is adapted to analyze both the incident photons and Compton backscattered photons having an energy level indicative of a backscattering angle of 180 degrees +/- a range parameter that is less than 30 degrees. For some applications, the apparatus includes more photon detectors than radiation sources.

For some applications, the control unit is adapted to map the feature by analyzing, in combination, incident photon counts and Compton backscattered photon counts measured by the plurality of photon detectors. For some applications, the control unit is adapted to map the feature by determining respective locations of the plurality of radiation sources, by analyzing, in combination, incident photon counts and Compton backscattered photon counts measured by the plurality of photon detectors. For some applications, the control unit is adapted to extrapolate a shape of the surface of the balloon responsively to the respective locations of the plurality of the radiation sources.

There is additionally provided, in accordance with an embodiment of the present invention, apparatus including:

a capsule, adapted to be swallowed by a subject, including a plurality of photon detectors;

an expandable structure, adapted, when expanded, to surround at least a portion of the capsule, and shaped, when expanded, so as to define a plurality of sites thereof that are not in direct physical contact with the capsule, the sites including respective radiation sources, adapted to emit radiation having an energy of at least 10 keV, wherein the photon detectors are adapted to detect photons generated responsively to the emitted radiation, the photons having an energy of at least 10 keV; and a control unit, adapted to analyze data regarding the photons in order to generate information useful for identifying a clinically-relevant feature of a gastrointestinal (GI) tract of the subject.

There is still additionally provided, in accordance with an embodiment of the present invention, apparatus for use with an object of interest, the apparatus including:

at least one radiation source, adapted to emit radiation having an energy of at least 10 keV;

at least one photon detector, adapted to detect photons having an energy of at least 10 keV;

a high Z agent, adapted to be placed between the radiation source and the object; and a control unit, adapted to analyze XRF photons emitted by the high Z agent responsively to the emitted radiation, and detected by the at least one photon detector, in order to estimate a distance between the radiation source and the object.

There is also provided, in accordance with an embodiment of the present invention, apparatus for use with an object of interest, the apparatus including:

at least one radiation source, adapted to emit radiation having an energy of at least 10 keV;

a contrast agent, adapted to be placed between the radiation source and the object; and a control unit, adapted to analyze Compton backscattered photons emitted by the contrast agent responsively to the emitted radiation, and detected by the at least one photon detector, in order to estimate a distance between the radiation source and the object.

There is further provided, in accordance with an embodiment of the present invention, apparatus for use with an object of interest, the apparatus including:

at least one photon detector, adapted to detect photons having an energy of at least 10 keV;

a radiolabeled material, adapted to emit radiation having an energy of at least 10 keV, and to be placed between the photon detector and the object; and a control unit, adapted to analyze detected photons emitted by the radiolabeled material, in order to estimate a distance between the photon detector and the object.

There is still further provided, in accordance with an embodiment of the present invention, a method including:

emitting, from within a gastrointestinal (GI) tract of a subject, radiation having an energy of at least 10 keV;

detecting, from within the GI tract, photons generated responsively to the emitted radiation, the photons having an energy of at least 10 keV; and analyzing data regarding the detected photons in order to generate information useful for identifying a clinically-relevant feature of the GI tract.

In an embodiment, the method includes administering an oral contrast agent to the subject. In an embodiment of the present invention, emitting the radiation includes orally administering to the subject a radiolabeled material that emits the radiation.

In an embodiment, emitting and detecting include orally administering a swallowable capsule to the subject, and emitting and detecting from the capsule. In an embodiment, detecting includes orally administering a swallowable capsule to the subject, and detecting from the capsule.

There is additionally provided, in accordance with an embodiment of the present invention, a method including:

detecting, from within a gastrointestinal (GI) tract of a subject, photons having an energy of at least 10 keV; and analyzing data regarding the detected photons in order to generate information useful for identifying a clinically-relevant feature of the GI tract.

There is still additionally provided, in accordance with an embodiment of the present invention, a method including:

emitting, from within a gastrointestinal (GI) tract of a subject, radiation having an energy of at least 10 keV;

detecting photons having an energy of at least 10 keV; and analyzing data regarding the detected photons in order to generate information useful for identifying a clinically-relevant feature of the GI tract.

There is also provided, in accordance with an embodiment of the present invention, a method including:

detecting, from a first plurality of points within a gastrointestinal (GI) tract of a subject, photons;

emitting, from a second plurality of points within the GI tract that surround the first plurality of points, radiation having an energy of at least 10 keV, wherein the photons are generated responsively to the emitted radiation and have an energy of at least 10 keV; and analyzing data regarding the detected photons in order to generate information useful for identifying a clinically-relevant feature of the GI tract.

There is further provided, in accordance with an embodiment of the present invention, a method including:

placing a high Z agent between a first site and a second site;

emitting, from the first site, radiation having an energy of at least 10 keV;

detecting photons having an energy of at least 10 keV; and estimating a distance between the first site and the second site by analyzing detected XRF photons emitted by the high Z agent responsively to the emitted radiation.

There is still further provided, in accordance with an embodiment of the present invention, a method including:

placing a contrast agent between a first site and a second site;

emitting, from the first site, radiation having an energy of at least 10 keV;

detecting photons having an energy of at least 10 keV; and estimating a distance between the first site and the second site by analyzing detected Compton backscattered photons emitted by the contrast agent responsively to the emitted radiation.

There is additionally provided, in accordance with an embodiment of the present invention, a method including:

placing a radiolabeled material, adapted to emit radiation having an energy of at least 10 keV, between a first site and a second site;

detecting photons having an energy of at least 10 keV; and estimating a distance between the first site and the second site by analyzing detected photons emitted by the radiolabeled material.

The present invention will be more fully understood from the following detailed description of embodiments thereof, taken together with the drawings, in which:

DETAILED DESCRIPTION OF EMBODIMENTS

Figure 1A:
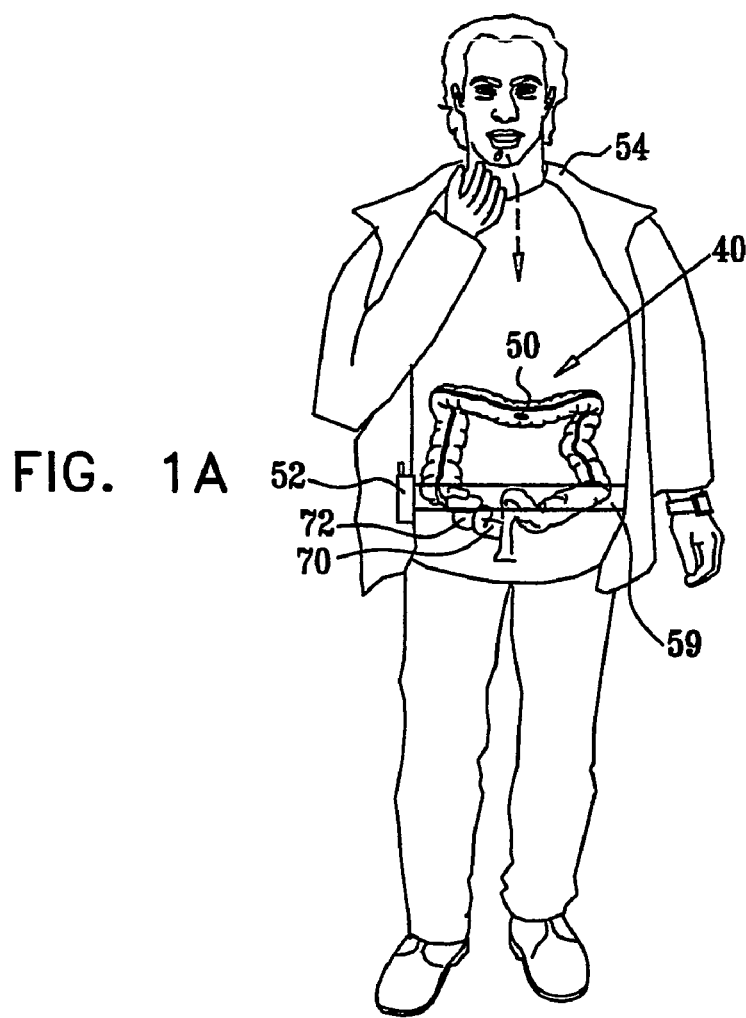
FIG. 1A is a schematic illustration of a screening system, in accordance with an embodiment of the present invention.

FIGS. 2A-D are schematic illustrations of apparatus for conducting an exemplary experiment that illustrates physical principles upon which some embodiments of the present invention are based, in accordance with an embodiment of the present invention. A container 12 is filled with a radio-opaque contrast agent 10 in liquid or low viscosity gel, and a reservoir 17 is placed below the container and filled with water 11. A small water-filled balloon 18 is placed at the bottom of the container. In this experiment, container 12 filled with contrast agent 10 simulates a colon filled with contrast agent, water-filled reservoir 17 simulates tissues and organs outside the colon, and water-filed balloon 18 simulates an anatomical abnormality, such a polyp.

In the experiment, a radiation source 14 and a radiation detector 16 are placed near each other. The open ends of a collimator 13 for source 14 and a collimator 19 for detector 16 are facing the liquid container. Radiation source 14 typically emits radiation at (a) a single emission energy level or (b) multiple emission energy levels, at least one of which is relatively low, and at least one of which is higher. Radiation detector 16 is configured to detect and count photons having an energy level (or levels, in the case of multiple energy level emissions) characteristic of photons that have been approximately 180-degree Compton backscattered by contrast agent 10, water of water-balloon 18, and water of reservoir 17.

Radiation source 14 and detector 16 are passed above container 12, maintaining a constant distance from the bottom thereof. At a plurality of points along the path of the source and detector, as shown in sequence from FIG. 2A to FIG. 2D, gamma or X-ray radiation count rates within one or more specific gamma and/or X-ray energy windows are logged (the count rates are shown in the figures on a log display 15).

Figure 2A:
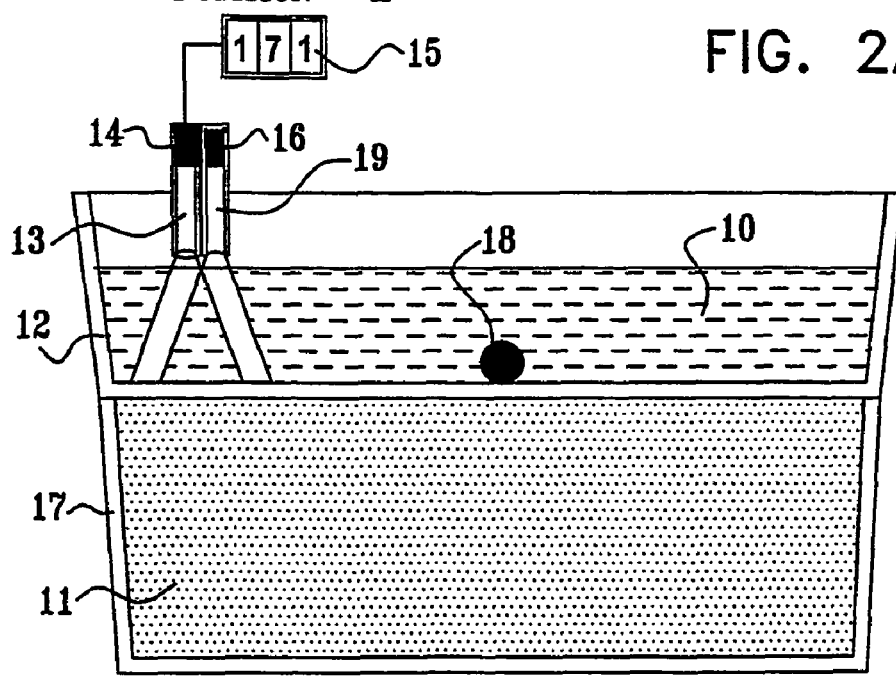
FIGS. 2A-D are schematic illustrations of apparatus for conducting an exemplary experiment that illustrates physical principles upon which some embodiments of the present invention are based, in accordance with an embodiment of the present invention.
Figure 2B:
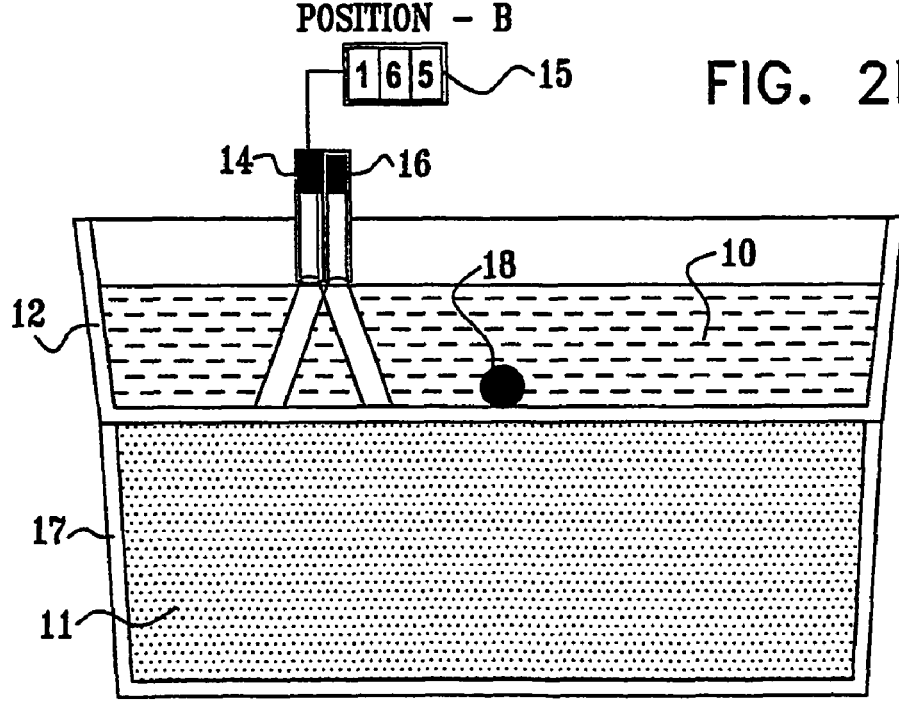
Figure 2C:
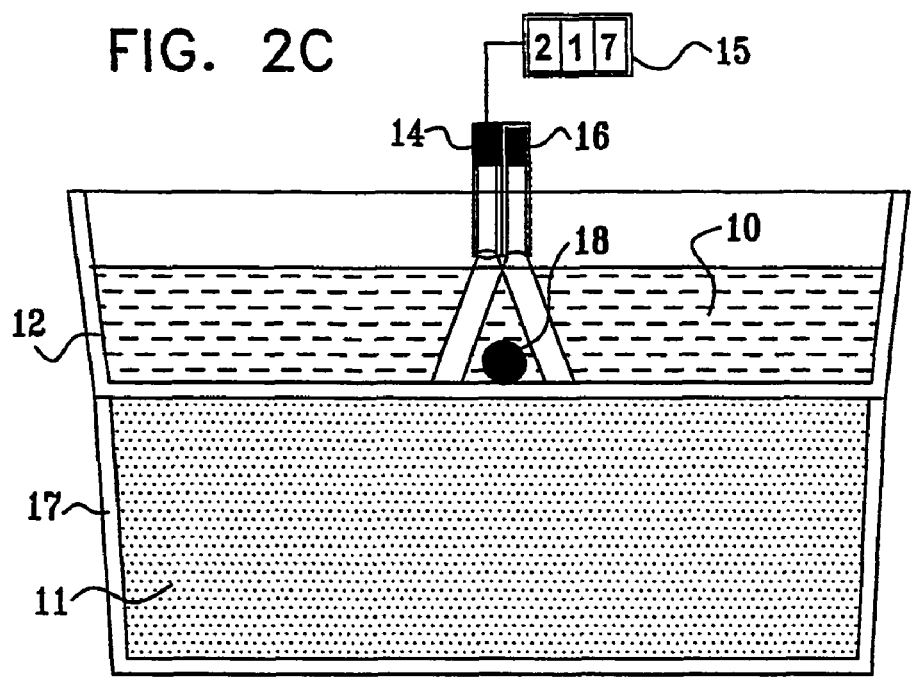
Figure 2D:
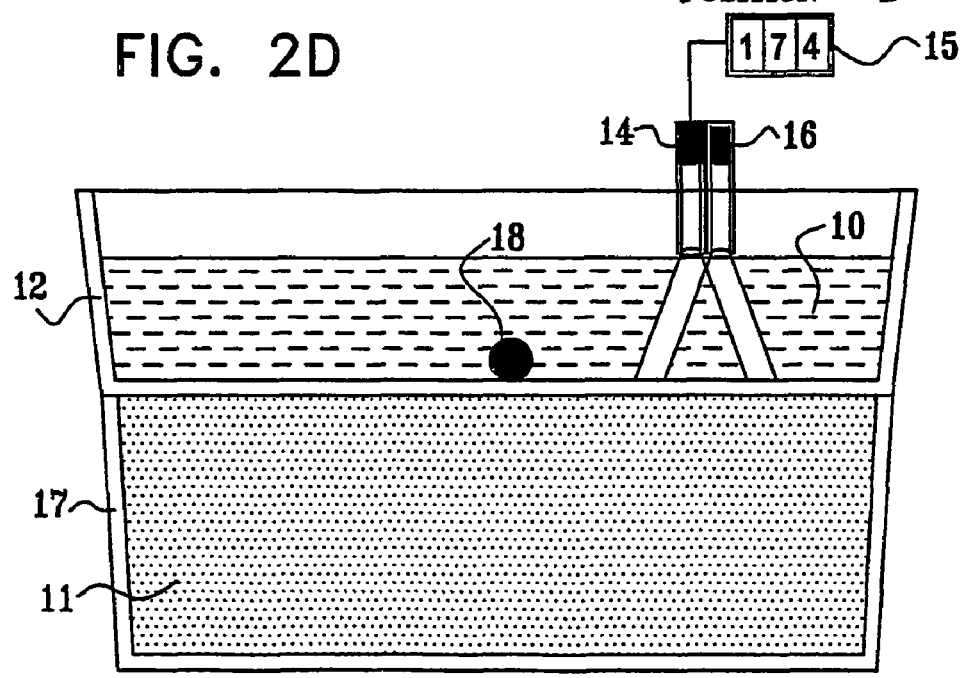
Figure 2E:
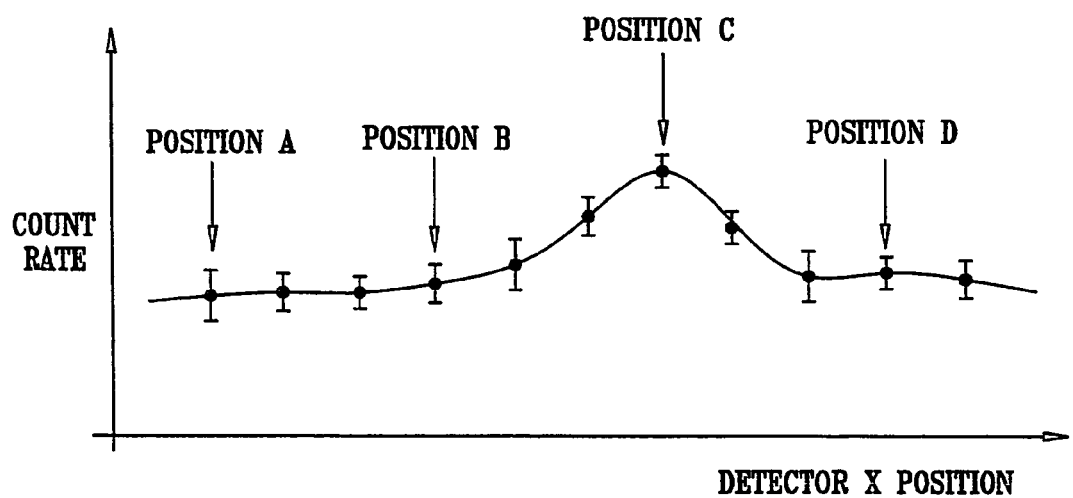
FIG. 2E is a graph showing exemplary experiment results of the experiment of FIGS. 2A-D, in accordance with an embodiment of the present invention.

FIG. 2E is a graph showing exemplary experiment results of the experiment described above with reference to FIGS. 2A-D, in accordance with an embodiment of the present invention. When radiation source 14 emits radiation of only a single energy level, as radiation source 14 and detector 16 pass above water balloon 18 (FIG. 2C), the count rate increases at the detector because the path of Compton backscattered photons interacts with a less radio-opaque volume. (In other words, balloon 18 is less radio-opaque than the contrast agent, and therefore allows the transmission of more of the photons.)

When radiation source 14 emits radiation at both a low energy level and a high energy level, as the source and detector pass above the balloon, the count rates of Compton backscattered photons from each of the radiation energy levels vary. In addition, a mathematical relationship (e.g., a ratio or difference) of count rates between the low energy windows and the high-energy windows varies. After the source and detector have passed the balloon (FIG. 2D), the count ratio returns to the level measured before the balloon was encountered. Counting is typically only performed within predefined energy windows that correspond to the energy levels of the Compton backscattered photons returning approximately 180 degrees relative to the emitted radiation for each of the photon energy peaks.

Figure 12:
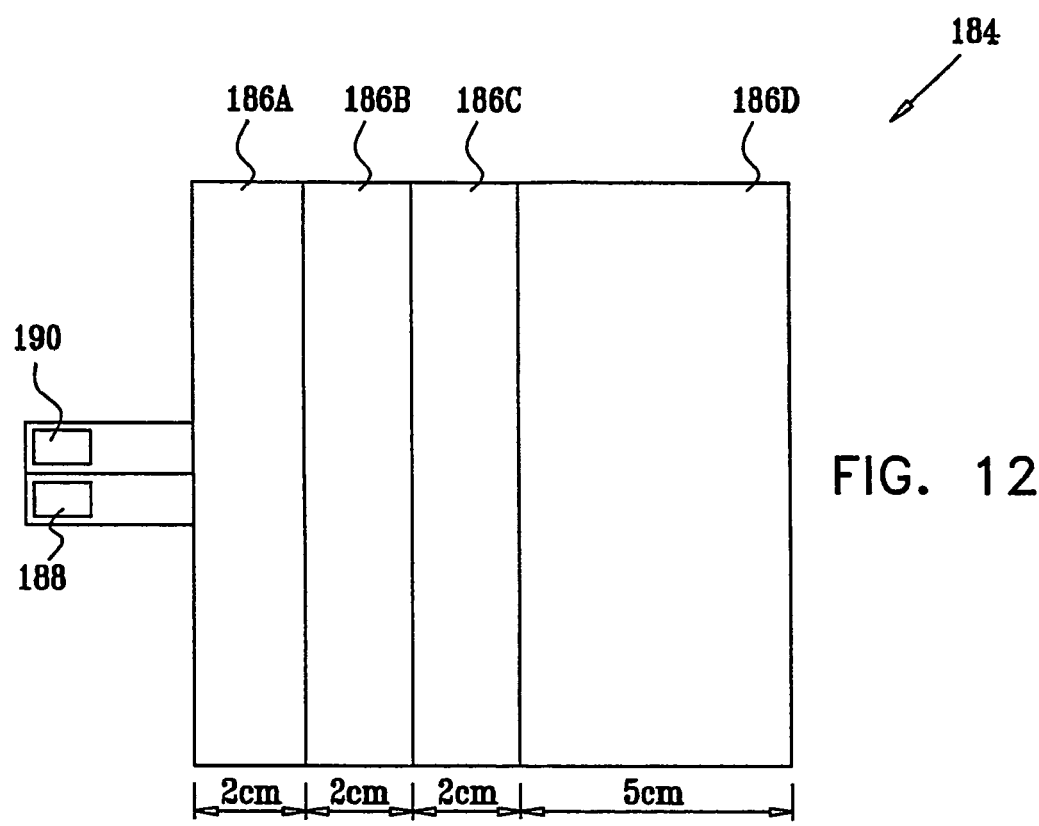
FIG. 12 is a schematic illustration of a tank used in an actual experiment performed by the inventors, in accordance with an embodiment of the present invention.

FIG. 12 is a schematic illustration of a tank 184 used in an actual experiment performed by the inventors, in accordance with an embodiment of the present invention. This experiment was similar to that described above with reference to FIGS. 2A-E. Tank 184 was divided into four compartments 186A, 186B, 186C, and 186D. Each of compartments 186A, 186B, and 186C had a depth of 2 cm, while compartment 186D had a depth of 5 cm. A collimated radiation source 188 and an adjacent collimated radiation detector 190 were placed next to tank 184 on the side at which compartment 186A was located.

Figure 13A:
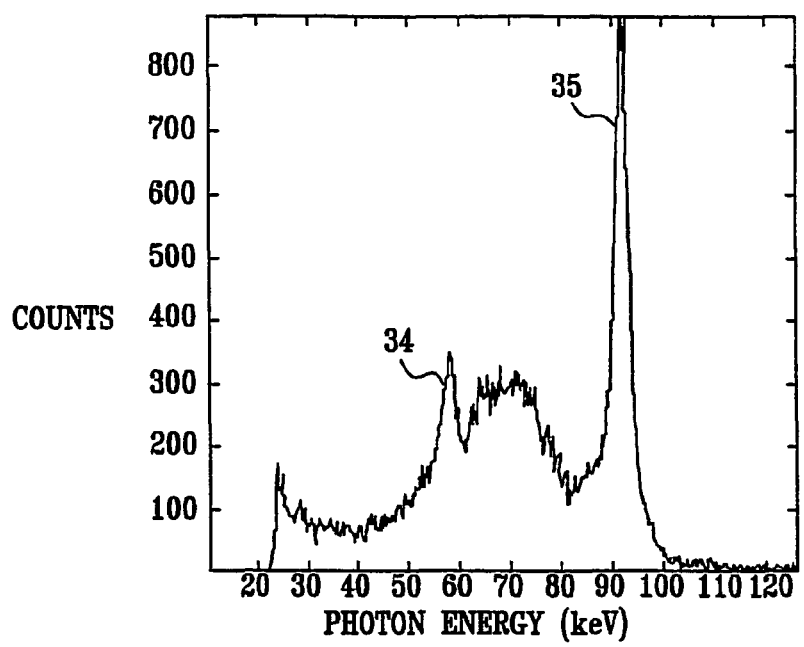
FIGS. 13A-C show actual experiment results from the experiment performed using the tank of FIG. 12, in accordance with an embodiment of the present invention.
Figure 13B:
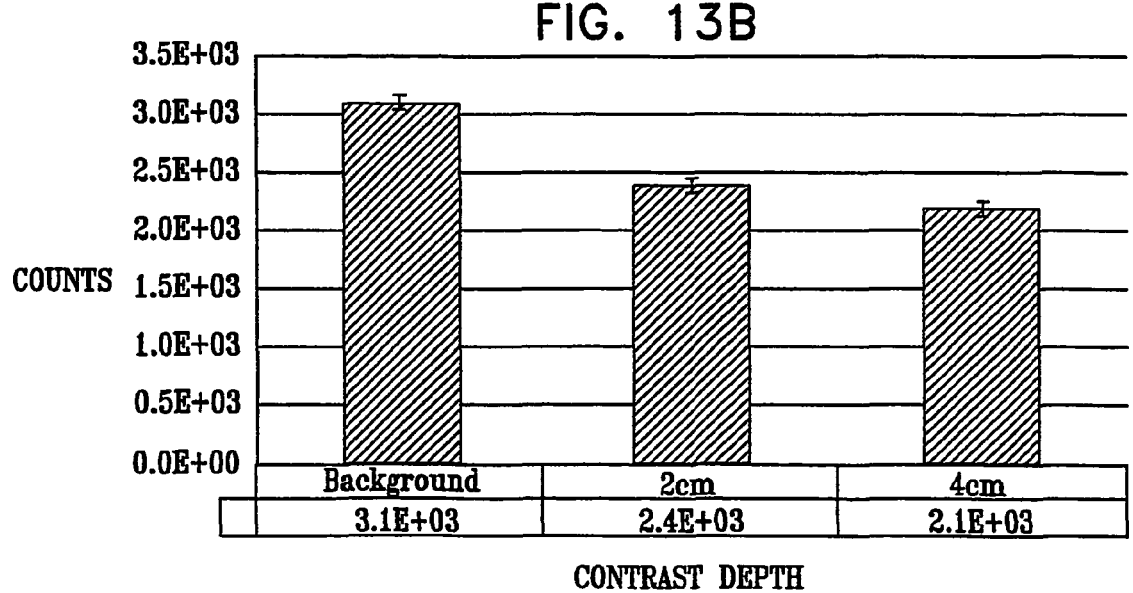
Figure 13C:
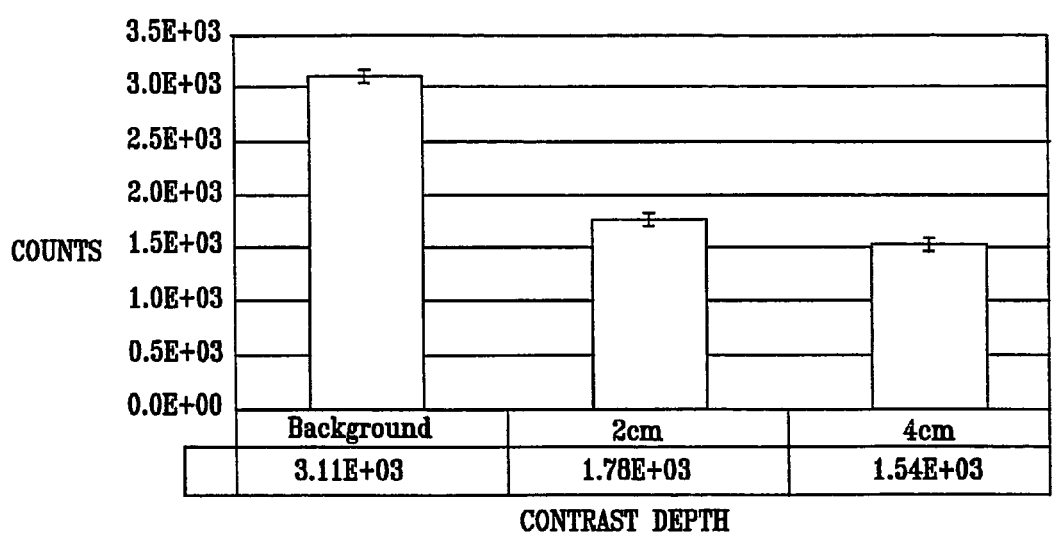

FIGS. 13A-C show results of the experiment conducted using tank 184, in accordance with an embodiment of the present invention. Radiation source 188 comprised the radioisotope Tc99m. FIG. 13A is a graph showing typical spectra detected by a radiation detector, in which a spectra line 35 is the 180-degree backscattering spectrum of 90 keV resulting from photons emitted from Technetium Tc99m (141 keV). (Spectra line 34 is the X-ray fluorescence (XRF) of lead that was used as the detector collimation.) The experiment was conducted twice, using Telebrix and barium sulfate (BaSO4), respectively, as contrast agents. FIGS. 13B and 13C show backscatter counts measured for Telebrix and BaSO4, respectively. During each performance of the experiment, an initial measurement was taken with all four chambers filled with water (i.e., no contrast agent); this measurement is shown by the bars labeled "Background" in FIGS. 13B and 13C. Chamber 186A was filled with the contrast agent, and a second measurement was taken (shown by the bars labeled "2 cm"). Subsequently, chamber 186B also was filled with contrast agent, and a third measurement was taken (shown by the bars labeled "4 cm"). As can be seen in the graphs, for both agents the use of additional contrast agent reduced the Compton backscattered photon counts. These experimental results are thus consistent with those shown in FIG. 2E, and show that the Compton backscattered radiation count is related to the round-trip distance that the photons travel through contrast agent.

Reference is again made to FIGS. 2A-E. As mentioned above, the photon count depends upon the depth of contrast agent through which the photons travel. This variability can be explained by the combination of three physical principles:

Compton scattered photons have lower energy than the incident photons, and the scattered photon energy depends on the scattering angle. See, for example, the above-mentioned article by Compton. Typically, only photons scattered at specific angles, based on their energies, are selected and counted.

The presence of water balloon 18 occupies volume that would otherwise be occupied by contrast agent 10. As a result, less absorption of radiation occurs. Absorption of radiation by the photoelectric process is strongly influenced by the photon energy. Therefore, photons with higher energies are less absorbed than photons of lower energy. Since the Compton scattering process is dependent on electron density, which is linearly dependent on the overall density, the Compton scattering is similar for the contrast agent and the water balloon. The photon absorption through the photoelectric process depends on Z^5 (atomic number to the 5th power). Thus, where there is less contrast agent due to the displacement of volume by the water balloon, there is a marked increase in photon flux that is detected by the radiation detector. In the case of multiple emission energies, the relationship (e.g., ratio or difference) between the detected high and low energy photons increases when the length of the path through the contrast agent increases.

Since the media is liquid or low viscosity gel, the concentration of contrast agent within a certain region can be assumed to be generally evenly distributed within this media given that sufficient time has passed after the introduction of the contrast agent.

Therefore, for a single energy photon emitting source, the relative flux of backscattered photons is inversely related to, e.g., inversely proportional to, the distance that the photons traveled through the contrast agent media during their entire flight from the radiation source and back to the radiation detector as Compton backscattered photons. For a multiple-energy photon emitting source, this technique for calculating the distance the photons traveled in the contrast media may also be used. In addition, the relationship (e.g., ratio or difference) between high- and low-energy photons received at the detector also indicates the distance the photons traveled in the contrast media. Because the relationship of the incident radiation generated by the radiation source is constant, any changes in this relationship are due to the unbalanced effect of predominantly photoelectric absorption in the contrast agent, which affects low energies substantially more than high energies. By logging this relationship, the presence of the water balloon is detected. This photoelectric absorption affects both the photons emitted by the radiation source and the backscattered photons.

Some embodiments of the present invention use the above principles and techniques to detect polyps and other anatomical deformations within the colon. Polyps, which are formed within the colon, sometimes harbor the seeds of cancer of the colon. It is therefore desirable to detect and remove polyps before cancer spreads from the inner surface deeper into the colon muscular structure, and subsequently to other parts of the body by metastasis. (As used herein, including in the claims, the "wall" of the colon or GI tract is to be understood as including any such polyps or other anatomical deformations thereof that may be present.)

In accordance with an embodiment of the present invention, the system described herein is used as a first-line screening procedure for early detection of colorectal cancer.

Reference is made to FIG. 1A, which is a schematic illustration of a screening system 40, in accordance with an embodiment of the present invention. System 40 typically comprises an ingestible capsule 50 and an external data-recording unit 52. For some applications, data-recording unit 52 is worn on the waist of a subject 54 (as shown in FIG. 1A) or elsewhere on the subject's body, such as the wrist (configuration not shown). Alternatively, for some applications, capsule 50 comprises an internal data-recording unit, and external data-recording unit 52 is not provided. In these applications, the data recorded by capsule 50 is retrieved after the capsule has been expelled from the body.

Figure 1B:
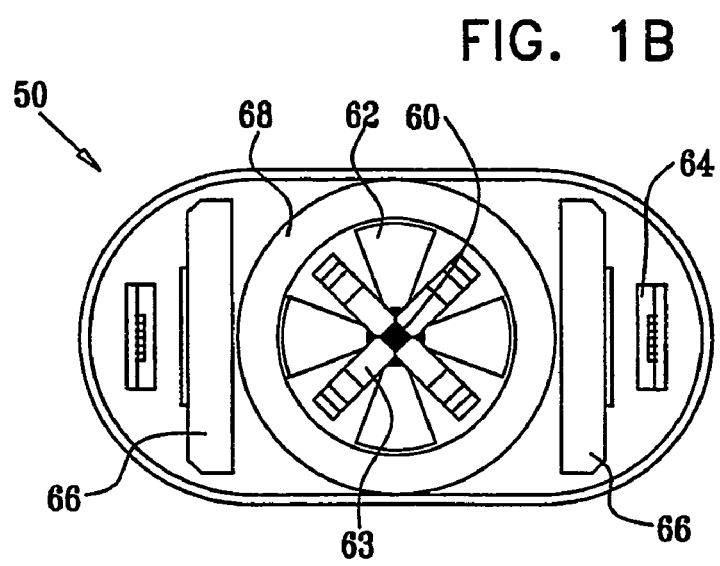
FIG. 1B is a schematic illustration of a capsule of the system of FIG. 1A, in accordance with an embodiment of the present invention.

Reference is made to FIG. 1B, which is a schematic illustration of capsule 50, in accordance with an embodiment of the present invention. Capsule 50 comprises at least one radiation source 60 adapted to emit gamma and/or X-rays (i.e., radiation having an energy of at least 10 keV), at least one gamma and/or or X-ray radiation detector 62, and, typically, at least one collimator 63 adapted to collimate the radiation produced by radiation source 60. For some applications, radiation source 60 comprises a radioisotope. Alternatively, radiation source 60 comprises a miniature radiation generator, such as described hereinbelow. Capsule 50 also typically comprises circuitry 64 (which, for some applications, includes a pressure sensor), a power supply 66, such as a battery, a wireless communication device for communicating with external data-recording unit 52 (communication device not shown), and a radiation shield 68.

Reference is now made to FIG. 1A. During a typical screening procedure using system 40, an oral contrast agent 70 is administered to subject 54. Contrast agent 70 is typically adapted to pass through a gastrointestinal (GI) tract 72 and be expelled with the feces, substantially without being absorbed into the blood stream. The contrast agent material may be similar to compounds used routinely for the study of the GI with X-rays, such as Barium sulfate liquid concentrate, iodine-based compounds, or other such materials. For some applications, additional appropriate contrast agents include Tantalum, Gadolinium, Thorium, Bismuth, and compounds of these materials. After the contrast agent is administered (e.g., several hours after the contrast agent is administered), subject 54 swallows capsule 50.

Capsule 50 travels through GI tract 72, emitting gamma and/or X-ray radiation. Beginning at a certain point in time, capsule 50 records the Compton scattered gamma and/or X-ray photons that strike radiation detectors 62. The count rate information received from each of the radiation detectors is typically stored together with a time stamp for that measurement. Within a time period typically of less than one second (e.g., several tens to several hundred milliseconds), it is assumed that the capsule and the surrounding colon wall and the contrast agent are in quasi-steady state. Taking small enough time intervals and integrating the counts over the small intervals allows for this quasi-steady-state assumption. The data may be stored in the capsule and sent by the capsule to the external recording unit from time to time, or after data-gathering has been completed.

In an embodiment of the present invention, radiation source 60 and detector 62 are arranged to "observe" the entire 4 pi squared sphere (or a portion of it) surrounding the capsule.

Figure 1C:
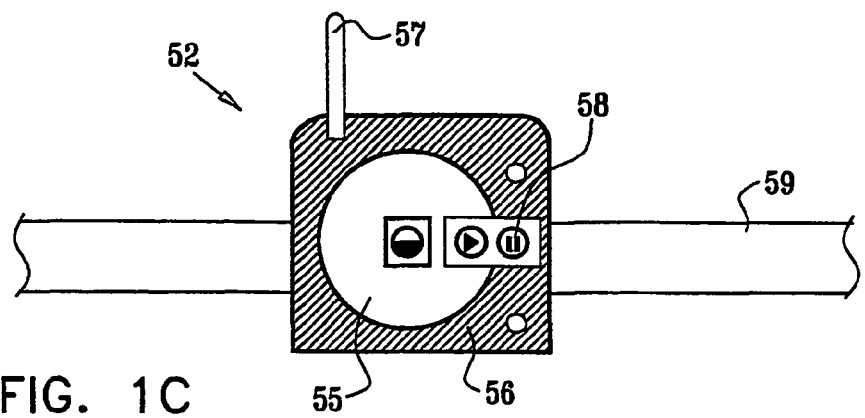
FIG. 1C is a schematic illustration of an external data-recording unit of the system of FIG. 1A, in accordance with an embodiment of the present invention.

Reference is made to FIG. 1C, which is a schematic illustration of external data-recording unit 52, in accordance with an embodiment of the present invention. Data-recording unit 52 comprises a receiver/memory unit 55, a support electronics/battery unit 56, an antenna 57, and user controls 58. Unit 52 also typically comprises a strap 59, such as a belt or wrist/arm strap, for coupling the unit to subject 54.

Figure 4:
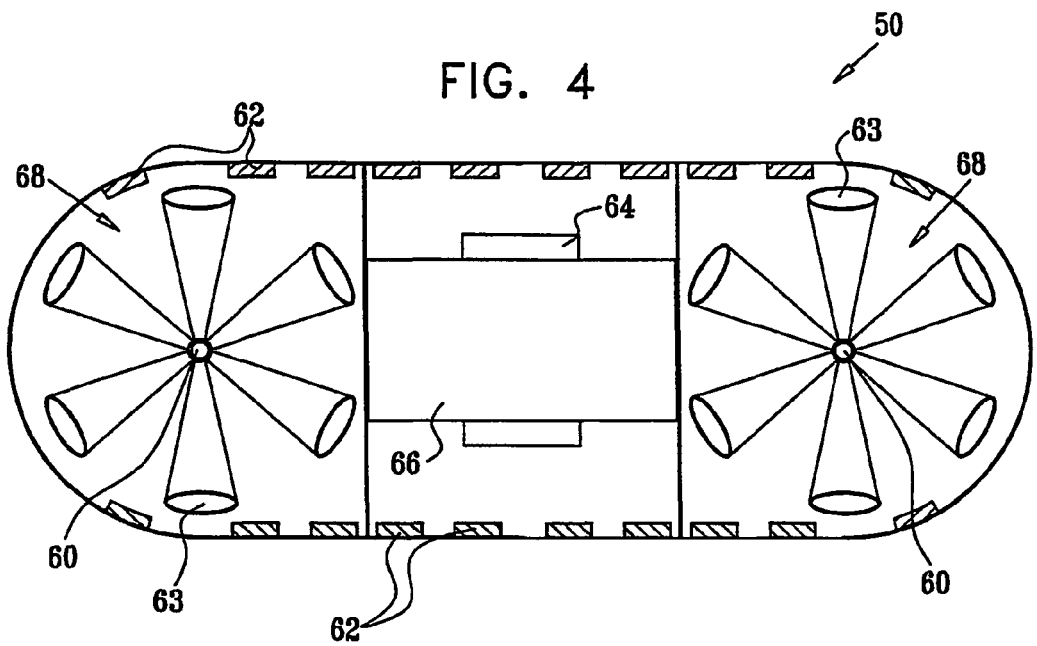
FIG. 4 is a schematic illustration of one configuration of the capsule of the system of FIG. 1A, in accordance with an embodiment of the present invention.

Reference is made to FIG. 4, which is a schematic illustration of one configuration of capsule 50, in accordance with an embodiment of the present invention. In this embodiment, capsule 50 comprises one or more radiation sources 60, one or more collimators 63, adapted to collimate radiation generated by radiation sources 60; and one or more radiation detectors 62, which are typically only slightly collimated or not collimated at all. Radiation sources 60 thus illuminate a confined solid sector (relative to the capsule). This is typically achieved by providing respective shields 68 for radiation sources 60, which prevent photons from being emitted in directions other than the preferred sector for each source. Shields 68 typically comprise a material having a high atomic weight and high specific density, such as lead, tungsten, or gold. Other arrangements for the sources, detectors and collimation may also be used, as appropriate, such as a cylindrical, spherical or other shield casing with the one or more sources.

In an embodiment of the present invention, a single source is placed within a spherical capsule, and the shell of the capsule is shaped such that multiple respective columns of photons outputted from the source are detected by one or more detectors on the surface of the capsule. In this embodiment, the detectors are typically not collimated.

In an embodiment of the present invention, radiation source 60 comprises a miniature X-ray generator, such as those described in one or more of the following above-mentioned references:

U.S. Pat. Nos. 6,134,300 and 6,353,658 to Trebes et al.

Haga A et al., "A miniature x-ray tube," Applied Physics Letters 84(12):2208-2210 (2004)

Gutman G et al., "A novel needle-based miniature x-ray generating system," Phys Med Biol 49:4677-4688 (2004)

Such a miniature X-ray generator or X-ray tube may be used for radiation source 60 instead of a radioisotope to illuminate the colon contents with X-ray photons. Turning such a generator on and off as needed typically reduces exposure of the subject to radiation. In addition, the energy range can be better controlled and the flux may be higher for the on periods without increasing subject total exposure.

In an embodiment of the present invention, apparatus is provided comprising:

an oral contrast agent such as barium sulfate or an iodine-based water soluble compound (such as Gastrografin, Telebrix, or other compounds described in the above-mentioned article entitled, "X-ray contrast medium";

a capsule, such as the capsule described hereinabove with reference to FIGS. 1B, 4, and/or 5, which is adapted to emit gamma and/or X-ray radiation and detect Compton scattered photons and other gamma and/or X-ray radiation. The capsule typically comprises: (a) one or more gamma and/or X-ray radiation sources and/or sources of beta electrons, such as T1201, Xe133, Hg197, Yb169, Ga67, Tc99, In111, or Pd 100, or (b) an X-ray generator, such as described hereinabove;

a recording unit, such as described hereinabove with reference to FIGS. 1A and 1C, which is adapted to receive RF signals from the capsule traveling within the GI tract; and data analysis and display software, such as described hereinbelow with reference to FIGS. 1D, 14A-C, and 15A-C. The software is adapted to receive the data from the recording unit, analyze the data, and display the processed data received from the capsule in such a manner as to allow the physician to assess the likelihood of the presence of a polyp or other anatomical deformation within the lumen of the tested individual. The software may run on a general-purpose computer, such as a personal computer, which is programmed in software to carry out the functions described herein. The software may be downloaded to the computer in electronic form, over a network, for example, or it may alternatively be supplied to the computer on tangible media, such as CD-ROM. Alternatively, the functionality of the software may be implemented in dedicated hardware logic, or using a combination of hardware and software elements.

Figure 9A:
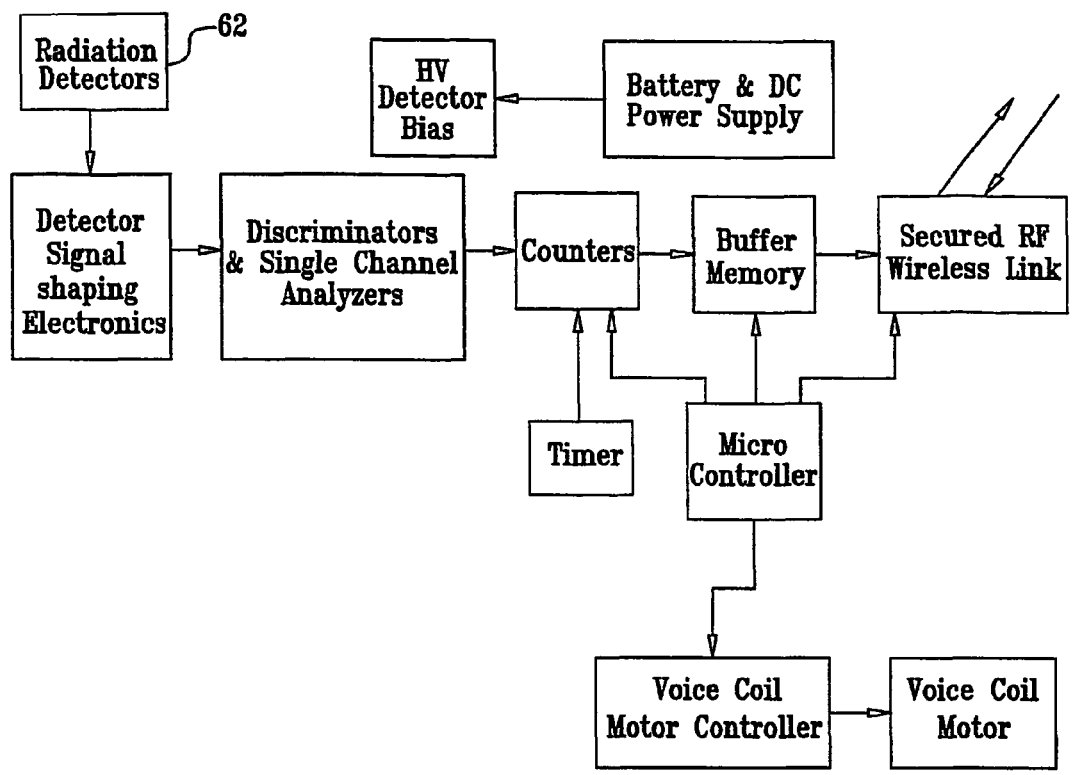
FIG. 9A is a block diagram schematically illustrating various functional blocks of the capsule of the system of FIG. 1A, in accordance with an embodiment of the present invention.

Reference is made to FIG. 9A, which is a block diagram schematically illustrating various functional blocks of capsule 50, in accordance with an embodiment of the present invention. In this embodiment, capsule 50 comprises one or more of the following components: (a) gamma and/or X-ray radiation detectors 62, which may comprise, for example, CZT crystals or scintillation crystals attached to photodiodes; (b) analog signal amplification circuits; (c) digital signal processing circuits; (d) digital memory circuits; (e) RF transmitting, receiving, and support circuitry; (f) calibration supporting circuitry; (g) internal timing circuitry; (h) a MEMS acceleration sensor chip and supporting circuitry; (i) a pressure sensor and supporting circuitry; (j) power supply circuitry including HV bias for the radiation detectors, and voltages for the MEMS; (k) a RF transmitter; (l) a RF receiver; (m) analog circuitry; (n) digital circuitry; and (o) a battery or some other power source, internal or external to the capsule.

Figure 9B:
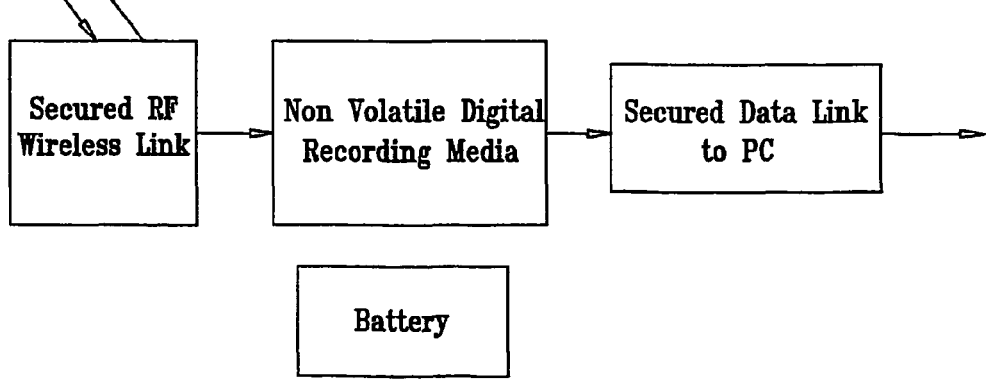
FIG. 9B is a block diagram schematically illustrating various functional blocks of the data-recording unit of the system of FIG. 1A, in accordance with an embodiment of the present invention.

Reference is made to FIG. 9B, which is a block diagram schematically illustrating various functional blocks of data-recording unit 52, in accordance with an embodiment of the present invention. In this embodiment, data-recording unit 52 typically comprises one or more of the following components: (a) RF communication circuitry; (b) non-volatile digital memory or other recording media adapted to safely store the received data; (d) communication circuitry for transferring the data to a computer; and (e) a power unit and supporting circuitry.

In an embodiment of the present invention, a method for detecting polyps and other anatomical deformations within the GI tract comprises: (a) placing a contrast agent within the internal space of the GI tract of a subject; (b) administering a capsule, such as capsule 50, to the subject; (c) detecting that the capsule has reached an area of clinical interest within the GI tract. For example, for detecting polyps or other anatomical deformations within the colon, the area of clinical interest is typically the colon or the lower ileum; and (d) responsively to the detection, activating the capsule.

As the capsule passes through the colon filled with contrast agent, radiation sources 60 emit gamma and/or X-ray photons, and each of radiation detectors 62 in the capsule detects Compton backscattered (approximately 180-degree) photons at the relative solid sector that the detector is observing. Each detector receives photons backscattered from a number of collimated sources, with the flux of photons depending on the relative geometry between the specific detector and the photon emitting collimators. The flux of backscattered photons is also dependant upon the volume of contrast agent that the backscattered photons encounter on their way to the detector, and this in turn is inversely related, e.g., inversely proportional, to the relative distance separating the collimator outer rim and the colon wall.

Since the relative geometry between the collimators and the gamma detectors is known, it is possible to estimate the distances from the collimator outer rims to the colon wall perpendicular to them, provided that there are sufficient gamma/X-ray detectors relative to the number of collimators. For some applications, the following algorithm is used to estimate these distances. Assuming a coefficient matrix C of scalars represents the geometrical coefficients between all emission collimators and all radiation detectors, and a vector X represents the measured values of count rates at the specific Compton backscatter energy window, then the problem to be solved can be expressed by the following equation:

$$C*X = d \qquad \text{(Equation 1)}$$

where C, X, and d are real, X and d are positive, and where the vector d represents the estimated ranges from each emission collimator to the colon wall perpendicular thereto. There are several known methods to solve the equation $C*X=d$, for example, by minimizing $C*X-d$. Other methods are known and may be applied to this problem.

Figure 10A:
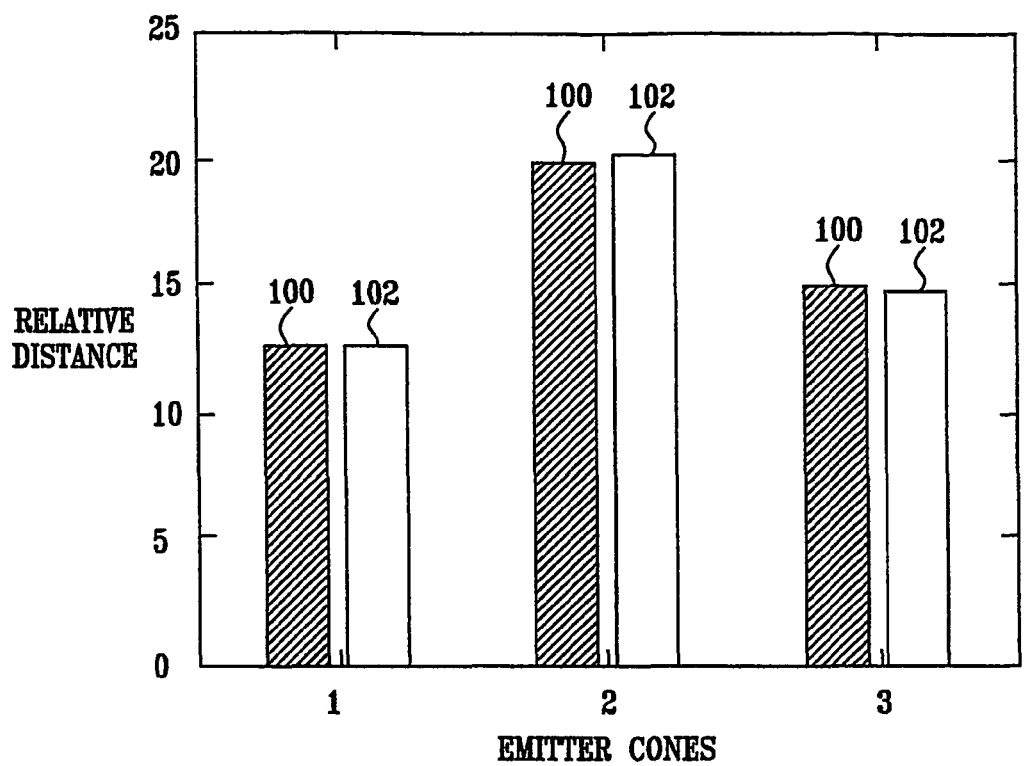
FIG. 10A is a graph illustrating the results of a simulation of the use of an algorithm for estimating distances, in accordance with an embodiment of the present invention.
Figure 10B:
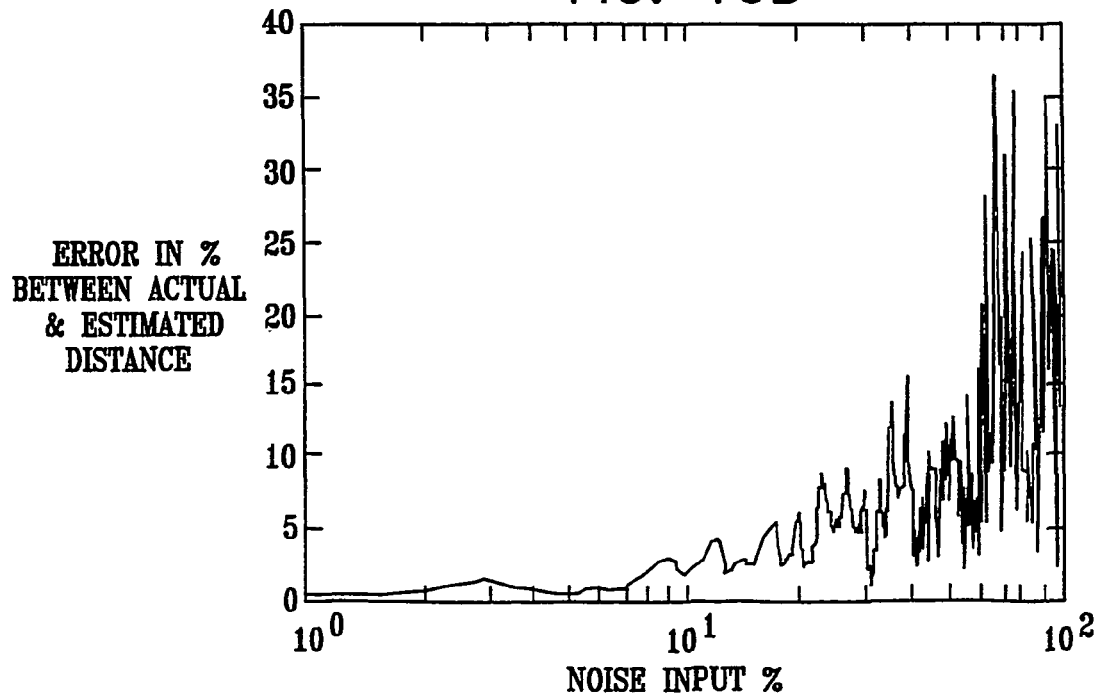
FIG. 10B is a graph illustrating the accuracy of the algorithm of FIG. 10A in the presence of varying percentages of Poisson noise, in accordance with an embodiment of the present invention.

FIG. 10A is a graph illustrating the results of a simulation of the use of this algorithm, in accordance with an embodiment of the present invention. Bars 100 represent simulated estimated distances as determined using this algorithm, and bars 102 represent respective actual distances. FIG. 10B is a graph illustrating the accuracy of this algorithm in the presence of varying percentages of Poisson noise, in accordance with an embodiment of the present invention.

In an embodiment of the present invention, detecting that the capsule has reached the area of clinical interest comprises detecting X-ray fluorescence (XRF) photons that are substantially different for the stomach, small intestine, and colon. As the capsule travels in the GI tract, the XRF count rate is measured and evaluated per time period. In the stomach, the XRF count rate is expected to be at a moderate level, as a portion of the oral contrast agent administered several hours earlier may still remain. As the capsule enters the small intestine, the XRF count is reduced significantly, because the capsule comes in contact with or nearly comes in contact with the small intestine wall, so there is insufficient space for a substantial amount of fluorescing contrast agent between the detector and the wall. Subsequently, as the capsule enters the colon, XRF counts increase, since the colon is filled with the contrast agent well-mixed along its length. (It is noted that some segments of small intestine are in close proximity of portions of the colon, such that when the capsule is in one of these segments, the XRF count may increase for some of the detectors because of contrast agent in the adjacent portion of the colon (and not because of local contrast agent in the small intestine). This increased XRF count persists until the capsule continues its travel and enters a portion of the small intestine that is not in such close proximity of the colon.)

Alternatively, detecting that the capsule has reached the area of clinical interest comprises using a pH sensor and/or a pH-sensitive coating for the capsule. For applications in which the area of clinical interest includes the colon, the pH sensor is typically configured to detect a reduction of acidity, and the pH-sensitive coating is configured to dissolve in the characteristic pH of the colon.

Further alternatively, for detecting that the capsule has reached the colon, the capsule comprises a trigger that is set to switch the capsule on once it passes near an externally-fixed sticker placed on the lower abdomen near the proximity of the entrance to the colon. Such a trigger may comprise, for example, an active oscillating circuit on the sticker. As the capsule comes close to the sticker, a passive resonant circuit in the capsule draws energy from the oscillating on the sticker, and this triggers the capsule to start operating. Similar devices are commonly used in anti-theft systems in stores and libraries.

Still further alternatively, for detecting that the capsule has reached the colon, the capsule comprises a pressure sensor that is adapted to measure pressure changes within the GI tract. As the capsule passes through the GI tract, pressure measurements are continuously monitored. In the stomach, pressure changes are generally infrequent, e.g., every few minutes. When pressure changes become more frequent and rhythmic, this may indicate that the capsule has entered into the small intestine, where it is expected to travel for 2-5 hours on average. Once the rhythmic pressure changes cease and less regular pressure waves and less frequent pressure waves are monitored, it is likely that the capsule has entered the large intestine where it is expected to remain for between 24 and 72 hours on average.

These techniques for detecting that the capsule has reached the area of interest may be utilized separately or in combination. When used in combination, information is typically correlated from a number of independent sensors as described above, and analyzed in order to ascertain that the capsule has reached the area of interest, e.g., the colon. (Alternatively, the capsule is in substantially continuous operation in the GI tract.)

In an embodiment of the present invention, the basic principle for the detection of polyps in the colon is based on the physical principles described in the experiments described hereinabove with reference to FIGS. 2A-E and 13A-C, and the use of the generally symmetrical properties of the colon muscular contractions and the general regular features of the inner colon lumen. For the detection of polyps, the capsule measures relative distances from each collimator outer rim to the colon wall surface. Then, at every point in time the algorithm searches and calculates a disk describing the maximal Compton backscattered flux that corresponds to a short axis of the colon (i.e., a diameter of the colon, when the colon is viewed in cross section). This disk describes the short axis of the colon at every point in time. Additional information that reinforces this calculation comes from analyzing a symmetrical cone with the axis centered around the maximal photon flux; this corresponds to a solid angle directed towards the short axis of the colon at every point in time. The algorithms then proceed to estimate the disk that is best described by the different range measurements by approximating a 2D elliptical spline that best fits these measurements. This in turn is the estimate of the colon section at the position of the capsule. Typically, as the capsule travels through the colon, it reconstructs aspects of the inner colon distances. For some applications, this calculation is performed in the coordinate system of the subject. For these application, the MEMS acceleration sensor chip in capsule 50 typically provides a reference to the direction of gravitational pull, and a second MEMS acceleration sensor chip coupled to an external surface of the subject (e.g., strap 59, described hereinabove with reference to FIG. 1C) provides a second reference for correcting for movements of the subject. Alternatively, for some applications, the calculation is performed in the coordinate system of capsule 50. In these applications, no reference is required, and the output includes distances relative to the capsule coordinate system.

Typically, after the capsule is expelled, the data are post-processed and presented to an expert viewer. For some applications, the data are presented as a series of cross sectional reconstructions to the viewer. An expert viewer is able to identify the irregular features that are not usually found in the inner colon lumen during a contraction of the colon muscles. Specifically, the system enables the detection of "bumpy" and irregular bulging features in the colon wall, which may be polyps or other suspect anatomical deformations.

Figure 1D:
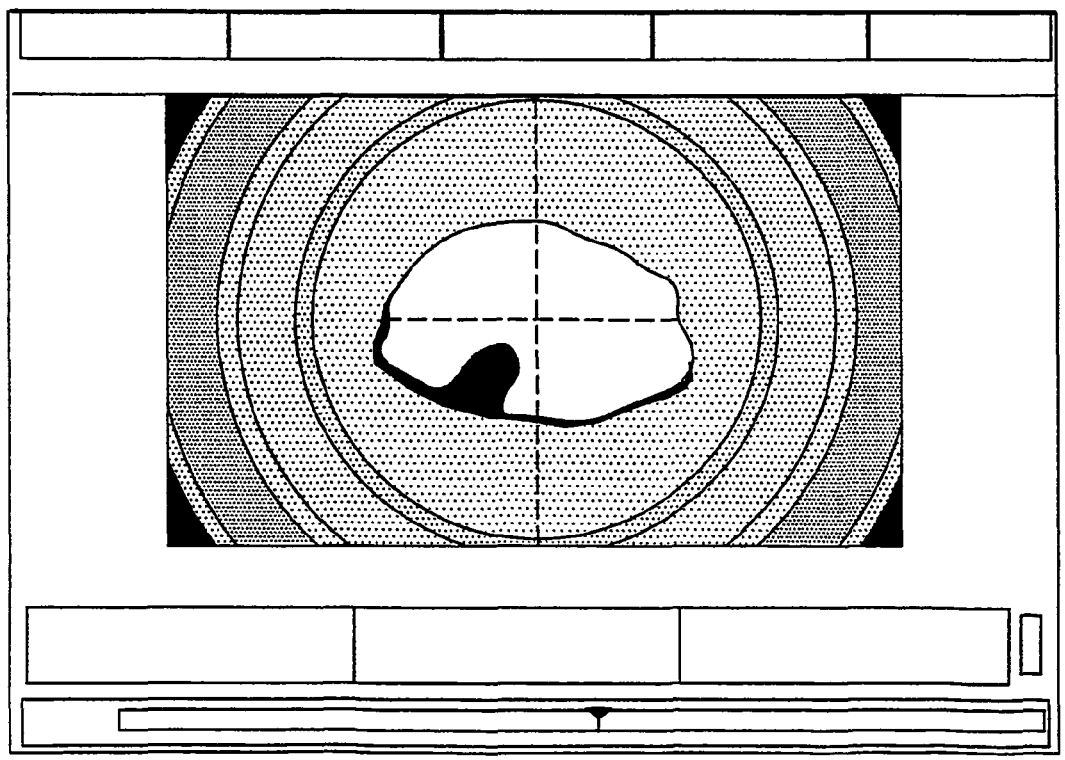
FIG. 1D is a schematic illustration of an exemplary graphical representation of a cross-sectional reconstruction of the colon, in accordance with an embodiment of the present invention.

Reference is made to FIG. 1D, which is a schematic illustration of an exemplary graphical representation of such a cross-sectional reconstruction of the colon, in accordance with an embodiment of the present invention.

In an embodiment of the present invention, the time derivative of the above data may be used for the reconstruction of the path that the capsule travels in the colon. Using the time derivative instead of the data itself or in conjunction with the data enables the viewer to better identify irregular features in the internal surface of the colon as the capsule traveled through the colon. In particular, this mode of analyzing the data enables the detection and differentiation between polyps and other features on the colon wall (such as haustra rings). Polyps show up in the time derivative view as relatively narrow tracks, while haustra rings appear as wide, tracks usually covering the entire 360 degrees around the capsule as it passes near them. (See FIGS. 14A-C and 15A-C, described hereinbelow.)

In an embodiment of the present invention, the data from the capsule may be presented to the physician in a graphical format (see FIGS. 14A-C and 15A-C, described hereinbelow) that does not give imaging information, but rather displays the information in a graphical representation that helps the physician to determine if there is a likelihood of a polyp or other anatomical anomaly that may harbor cancer and require colonoscopy.

For applications in which radiation source 60 emits photons having two or more different energies, the basic analyzed data unit may be a relationship (e.g., a ratio or difference) between the high-energy counts and the low energy counts. Alternatively or additionally, the basic analyzed data unit is the count for each of the energy windows.

In an embodiment of the present invention, the ratio between the high energy count rate and the low energy count rate backscattered from the colon contents and beyond is used to calibrate the actual distance of the capsule from the colon wall. This is possible because the ratio of the photon flux at the different energies is related to, e.g., proportional to, the actual distance. This property is especially useful since the concentration of the contrast agent may change as the capsule travels from the right colon, where the colon contents are fluid, to the left colon and the rectum, where the colon contents are usually less fluid, or even semi-rigid. Therefore, the average flux of photons per centimeter depth of contrast agent decreases as the concentration of the contrast agent increases. (Water flows out of the colon; hence the contrast agent concentration in the colon increases, because the agent does not leave the colon.)

In an embodiment of the present invention, a capsule such as capsule 50 is adapted to detect Compton backscattered photons, typically those photons emerging from a backscattering process of 180 (+/−20 to 30) degrees relative to the incident photons, depending on the detector energy resolution and the detector collimation (if collimated). For multiple energy window applications, the count rates for different energy windows are used as the basic data for the imaging process. In particular, for each detector, the electronics associated with its dedicated channel sum the number of photons that hit the detector at each of the predefined energy windows according to Compton backscattered energy principles. (Other energy windows are set to detect XRF photons coming from the contrast agent that is being illuminated.)

In this embodiment, capsule 50 implements an algorithm that may be understood by way of analogy with compound eyes of insects. Such eyes do not have a single focusing lens, but instead have a multitude of optical sensors arranged in a portion of a hemisphere. Insects with compound eyes are extremely shortsighted, seeing only a few millimeters in front of them. But their eyes are well adapted to detect motion at farther distances, and to detect the vector direction and morphology of the moving object. For example, these capabilities allow a flying dragonfly to detect a flying mosquito several meters away from it, and allow insects such as the bee to fly at high speed through a dense forest without colliding with branches.

For a capsule adapted to travel in the GI tract, it is generally difficult to fit a large array of detectors and suitable collimation apparatus in order to reconstruct a high-resolution image. Therefore, the situation is similar to that of an insect having to "recognize" morphologies using limited detector resources. In an embodiment of the present invention, the detectors are arranged in the capsule to "view" the hemisphere or part of the hemisphere surrounding the capsule. Nevertheless, the number of detectors is typically limited to less than 100, e.g., less than 40, the upper bound of the number being set by (a) the minimum size of any given detector that still provides reasonable signal to noise, and (b) the maximum number of independent signal channels that can be reasonably accommodated in the small available space of the capsule. Additionally, in order to best utilize the relatively few photons that are available from the Compton backscattering process and lack of space on the capsule, the detectors are typically arranged without or with very slight collimation. Hence, each detector "sees" a relatively wide angular view, and the overall static spatial resolution is compromised to some extent, like the case of the insect compound eye. Unlike in the case of the insect in which the resolution is set by the viewing angle of a single optic detector, in the case of the capsule, the capsule's "viewing" resolution is determined by the collimations of the radiation source(s).

As in the case of the insect, the capsule is "shortsighted," being able to compose a static image only from a few millimeters distance. However, like the insect with its compound eyes, the capsule is able to detect curves, haustra rings and polyps while moving through the colon. Typically, but not necessarily, the detection of polyps and other morphologies is done offline, by using the data gathered by the capsule as it travels through the colon.

Reference is made to FIGS. 14A-C and 15A-C, which are schematic illustrations of surfaces representing morphologies of the GI tract, generated in accordance with an embodiment of the present invention. A dynamic tracking algorithm is provided for detecting polyps in the GI tract, such as in the colon, and discriminating them from other morphologies normally found in the colon, such as curving colon walls, haustra rings, and folds of the colon. This algorithm makes use of movement of the capsule within the colon to detect and separate the morphology of polyps from the morphologies of the other normal structures in the colon.

In this embodiment, the emitted radiation is typically configured so as to "illuminate" all or a portion of the volume surrounding the capsule. Alternatively, the collimation on the emitted radiation is configured to selectively illuminate certain sectors of the volume surrounding the capsule while leaving other sectors unilluminated. This latter configuration may serve to better detect anatomical formations within the colon as the capsule moves, detecting the objects of interest as they move from "shadow" to "light."

In the following description of the dynamic tracking algorithm, for the sake of simplicity, it is assumed that the radiation detectors are spread over a 2D rectangular surface. It is also assumed that the data from the detectors are mapped onto a 2D rectangular surface where each detectors data are represented by a measured reading of a property such as the count rate per integration time in a certain energy window corresponding to the Compton backscattered photon energy window. In this manner, the 3D internal colon lumen is mapped onto the 2D rectangular surface.

At a first step of the dynamic tracking algorithm, for every subdivision on the 2D representing surface, a relative distance that each collimator "sees" is calculated, e.g., using the matrix algorithm of Equation 1, described hereinabove. Surfaces 120A, 120B, and 120C of FIGS. 14A, 14B, and 14C, respectively, and surfaces 122A, 122B, and 122C of FIGS. 15A, 15B, and 15C, respectively, are exemplary representations of such a relative distance-indicating surface, at respective points in time.

At a second step of the algorithm, a difference is calculated between the reading representing the subdivision and the respective readings representing all of the neighboring subdivisions (up to 6 neighbors on the 2D surface).

At a third step, a threshold is calculated, e.g., +/−σ relative to the subdivision value, based on a Poisson distribution. For example, if Nij is the reading at a subdivision ij (after the analysis described in the first step), the threshold will be one sigma (i.e., +/− the square root of Nij). Only readings at least one sigma from the subdivision value are used at the fourth step, described immediately below.

Figure 14A:
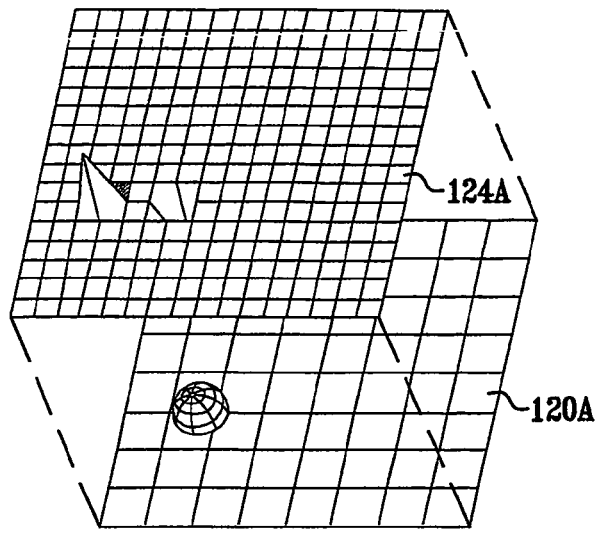
FIGS. 14A-C and 15A-C are schematic illustrations of surfaces representing morphologies of the GI tract, generated in accordance with an embodiment of the present invention
Figure 14B:
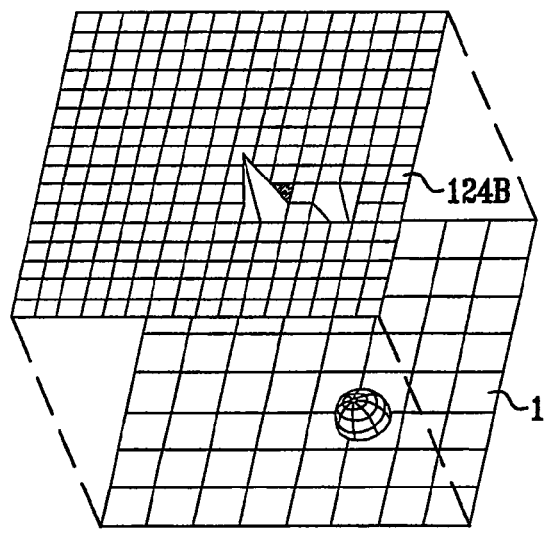
Figure 14C:
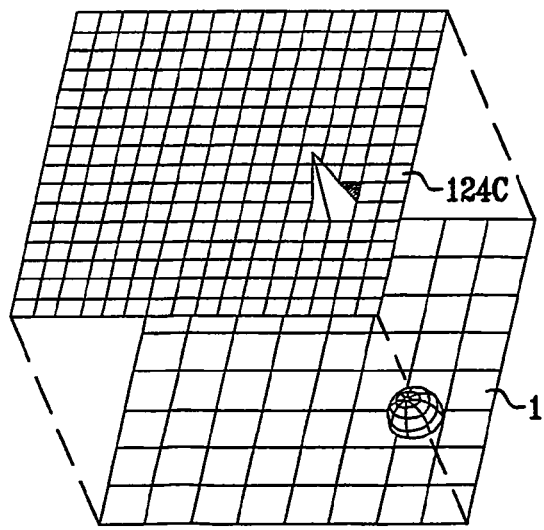
Figure 15A:
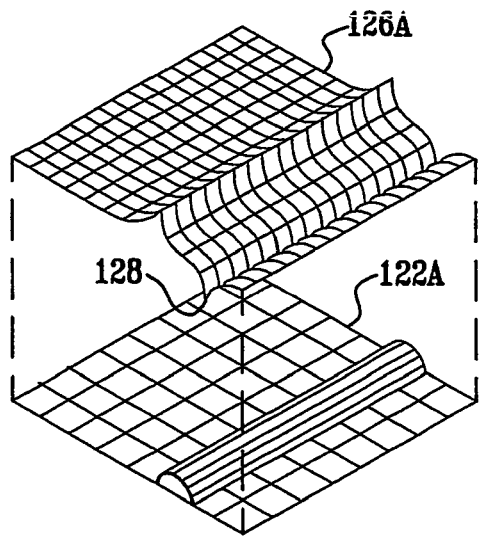
Figure 15B:
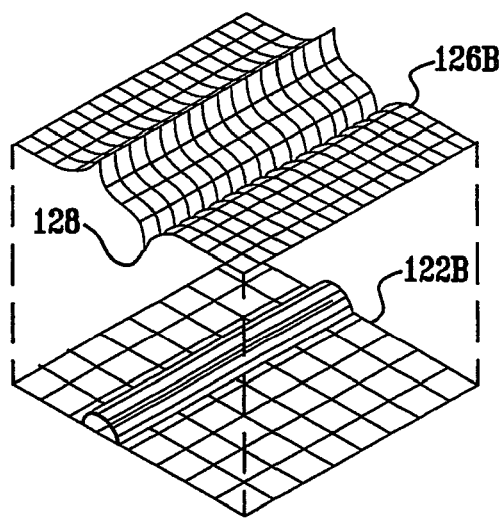
Figure 15C:
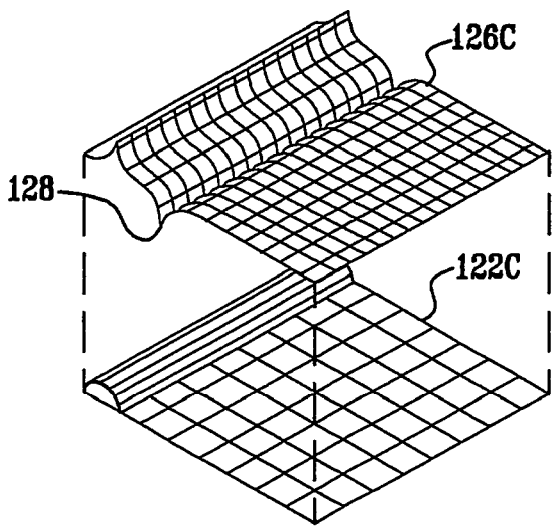

At a fourth step, a new 2D surface is plotted, in which the pixels represent differences between the subdivisions of the first 2D map (i.e., of surfaces 120A-C and 122A-C of FIGS. 14A-C and 15A-C, respectively). The outcome of this representation is a series of 2D morphologies in time that represent time derivatives outlining the movement of the capsule within the colon and showing different morphologies as the capsule travels. Surfaces 124A, 124B, and 124C of FIGS. 14A, 14B, and 14C, respectively, and surfaces 126A, 126B, and 126C of FIGS. 15A, 15B, and 15C, respectively, are exemplary representations of surfaces representing such differences, at respective points in time. For example:

- The morphology of a moving front (made up of a few correlated routes) is a line, such as a line 128 of FIGS. 15A-C.
- The morphology of a moving front that has cylindrical symmetry (in the 3D capsule space) appears as a linear ridge across the 2D difference space, such as ridge 130 of FIGS. 15A-C. Such a moving front may be related to wall motion or capsule motion in relation to the walls.
- A moving object that has isolated morphology may be related to polyps or other anatomical anomalies, as shown in FIGS. 14A-C.

At a fifth step of the algorithm, these 2D difference maps are shown as an animated series to the expert viewer in order to assist him to evaluate possible anomalies, such as polyps.

For some applications, the algorithm uses an autocorrelation function based on readings from detectors to estimate local 3D movements of the capsule. Use of such an autocorrelation function generally improves signal to noise. This information can then be used to correlate readings from adjacent subdivisions and hence to increase the integration times by estimating the readings based on a number of integration time periods rather than using single integration times. This increase in integration time by averaging correlated readings generally reduces noise. Data from the MEMS acceleration sensor chip (FIG. 9A) may also be used for this correlation, or as a confirmatory measurement.

The dynamic resolution provided by this algorithm generally allows the resolution of polyps at relatively large distances from the capsule, even using a relatively small number of detectors. This is the case even though the relatively small number of detectors are not collimated or are slightly collimated (and hence they overlap in their field of view), which, without the use of such an algorithm, would generally result in a relatively low static resolution (which is determined by radiation source collimation).

Other algorithms which make use of dynamic analysis may be used to detect polyps or other anatomical anomalies in the colon and discriminate between them and normal colon wall movements (e.g., colon muscle contractions) and capsule movements within the colon. In particular, algorithms that use dynamic analyses analogous to those described may be adapted for use with the embodiments described above, to enhance robustness and improve noise immunity to spatial and temporal variations. In particular, dynamic analysis may be used in conjunction with the static analysis to improve the detection and evaluation of abnormalities such as polyps.

Figure 5:
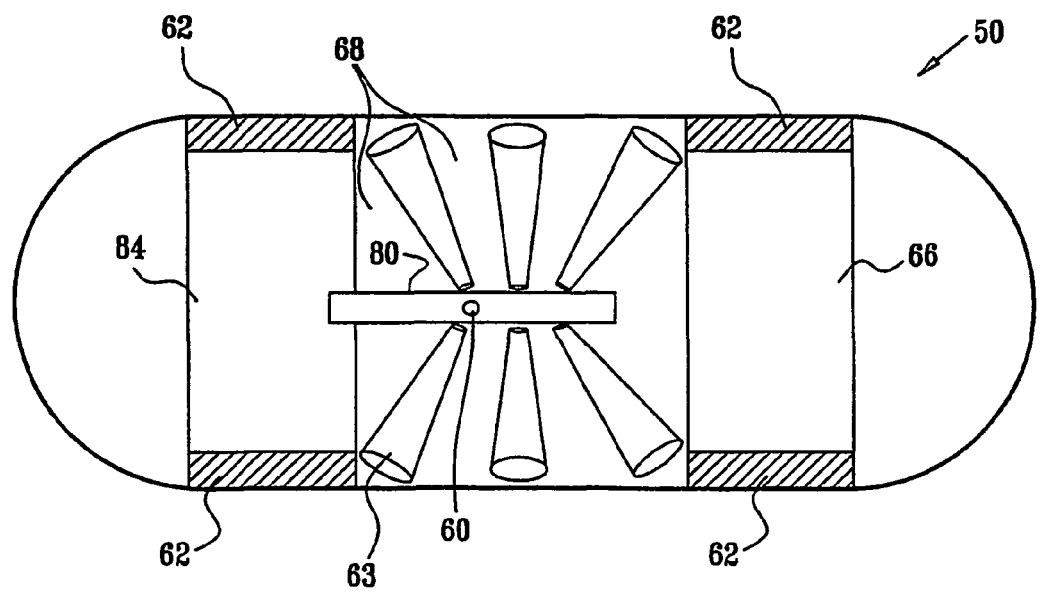
FIG. 5 is a schematic illustration of a time-multiplexed configuration of the capsule of the system of FIG. 1A, in accordance with an embodiment of the present invention.

Reference is made to FIG. 5, which is a schematic illustration of a time-multiplexed configuration of capsule 50, in accordance with an embodiment of the present invention. In this embodiment, capsule 50 comprises at least one radiation shield 68. The capsule is configured such that shield 68 blocks radiation emitted from radiation source 60 a portion of the time that the capsule is in the GI tract. For some applications, this partial blocking is achieved by moving shield 68. Alternatively or additionally, the blocking is achieved by moving radiation source 60. For some applications, radiation source 60 is coupled to a moving rod 80. During a rest phase, at times when the capsule is not intended to gather data, radiation source 60 is positioned behind shield 68 so that the amount of radiation that escapes towards the subject's body is minimal. During an operational phase, during which capsule 50 gathers data, rod 80 is moved back and forth, such as by a low power actuator 84 (for example, a voice coil linear actuator, or a piezoelectric linear actuator motor). The motion of rod 80 exposes radiation source 60 to different collimators 63, causing radiation source 60 to illuminate, at different times, different angular sectors of the sphere surrounding the capsule. Detectors 62 detect the Compton backscattered photons or the X-ray fluorescence photons from the colon contents including media, time-synchronized to the radiation source position.

For some applications, radiation source 60 comprises an isotope, e.g., Tl201, I111, I131, Ga67 Tc99m, or Pd 100. For some applications, rod 80 comprises a heavy metal, such as tungsten, lead, or tantalum. For some applications, shield 68 comprises a high Z material, such as tungsten, gold, or tantalum.

Using these techniques, the system resolution may be controlled by adjusting the "illumination" volumes. For example, a relatively high intensity radiation source may be placed in a capsule, and by controlling the collimation angle of the source, enable a very narrow high resolution observed volume. In this configuration, the overall radiation exposure for the subject is still relatively small.

The physiology and anatomy of the human colon is such that most of the time (during an average period of 24-72 hours) the contents of the colon are stationary, mixing a little from time to time but not moving forward. Once every few hours, a contraction starts that generates pressure within the colon (up to an average of 200 mmHg) squeezing material forward towards the anus. To minimize subject radiation exposure, the motorized back-and-forth movement of radiation source 60 is typically only activated when the capsule senses intra-lumen pressure buildup indicative of imminent mass movement within the colon, and/or when the capsule senses angular change, using the MEMS acceleration sensor chip, indicative of possible imminent motion of the capsule. During periods in which the capsule does not sense any pressure or change in tilt angle, and the XRF readings for the detector(s) closest to the colon wall are at steady state, radiation source 60 is stationary at the center of shield 68.

The motorized back-and-forth movement of radiation source 60 causes the radiation source to emit gamma or X-ray radiation through collimators 63 as the radiation source passes back and forth behind shield 68. Collimators 63 are arranged such that at any given time, only a predetermined subset of the collimators emit radiation. Exposing the radiation source only when the capsule is expected to collect data generally reduces the amount of radiation to which the subject is exposed.

In an embodiment of the present invention, actuator 84 and rod 80 are arranged such that rod 80 moves according to the dynamics of a forced mechanical oscillator. In this arrangement, rod 80 is coupled to at least one spring (spring not shown) such that the combination of the rod and spring forms a mechanical oscillator having a specific resonance frequency. At or near this frequency, the energy required to move rod 80 is minimal. Actuator 84 supplies the energy lost to friction. At both ends of the movement of the rod, the rod slows. The rod, spring, and collimators are typically arranged such that the radiation source is exposed to the openings of the collimators at the locations at which the rod slows.

In an embodiment of the present invention, a processing unit is incorporated within the capsule so that limited data analysis can be done within the capsule in real time. In particular, the capsule may calculate the autocorrelation function of the measured data and combine this information in order to determine if the capsule is moving within the colon due to gravitational or other external forces other than pressure-induced mass movements. In particular, the combination of the MEMS accelerometer and the autocorrelation function can help determine if the capsule is stationary or moving within the colon. The capsule accordingly continues to operate the movement of the radiation source until the capsule comes to rest.

In an embodiment of the present invention, shield 68 may comprise, at least in part, a magnetic material, such that the shield functions as part of actuator 84 (for example, when the actuator comprises a voice coil actuator). In this embodiment, a dedicated magnet is generally not needed.

In an embodiment of the present invention, the contrast agent is mixed with ferromagnetic particles, e.g., spherical particles. When the capsule enters the colon, these particles are magnetically attracted to the capsule, and form an enlarged mass that travels with the capsule, thereby slowing the capsule and increasing the probability of detection of polyps. For some applications, shield 68 comprises an electromagnet, which may be turned on or off so as to permit or force the ferromagnetic particles to separate from the capsule.

Reference is now made to FIGS. 6A-E, which are schematic illustrations of capsule 50 coupled to an inflatable balloon 140, in accordance with respective embodiments of the present invention. Inflation of balloon 140 around capsule 50 typically moves the capsule away from the outer surface of the balloon, toward the center of the balloon. As a result, the capsule is positioned closer to the center of the colon lumen. Such positioning generally improves system resolution on all sides of the capsule for the detection of polyps and other anatomical anomalies. Techniques for detection of anatomical anomalies and polyps using the balloon configurations are essentially the same as those for embodiments that do not comprise a balloon.

In these embodiments, balloon 140 is adapted to inflate when capsule 50 reaches an area of clinical interest, typically the colon. Capsule 50 typically detects its arrival in the colon using techniques described herein. For some applications, for inflation, balloon 140 contains or is coupled to a material that releases a gas (e.g., $CO_2$) or gel when the material comes in contact with water of the colon contents. For example, balloon 140 may comprise such a compound 142 positioned on an external surface of the balloon. Compound 142 is exposed both to the contents of the colon and the interior of the balloon. Other techniques for inflating the balloon will be apparent to those skilled in the art who have read the present application, and are within the scope of the present invention.

For some applications, balloon 140 comprises a release valve 144, configured to begin slowly dissolving when the valve comes in contact with water of the colon contents. Valve 144 is typically configured to dissolve over a predetermined period of time somewhat longer than the expected time required for the passage of the capsule through the colon. The dissolving of valve 144 allows gas contained in balloon 140 to escape from the balloon, thereby deflating the balloon. This mechanism ensures that the capsule and balloon will not undesirably block the passage of material in the colon.

Figure 6A:
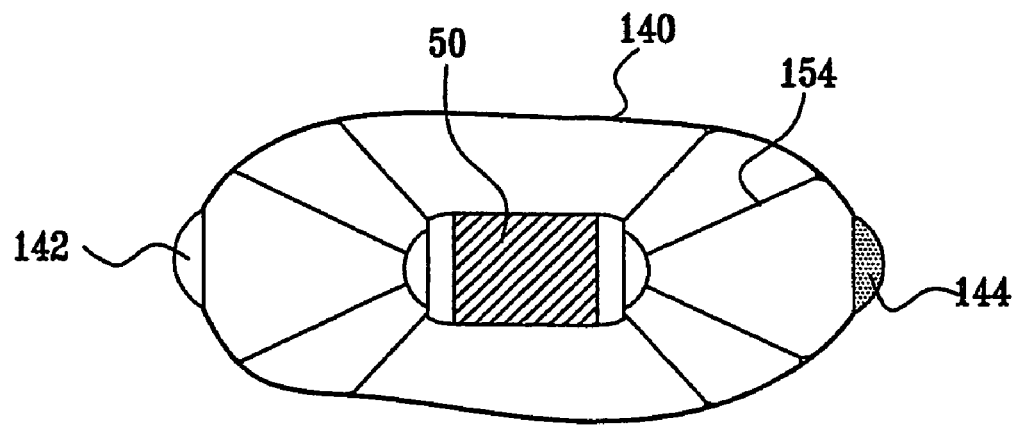
FIGS. 6A-E are schematic illustrations of the capsule of the system of FIG. 1A coupled to an inflatable balloon, in accordance with respective embodiments of the present invention.
Figure 6B:
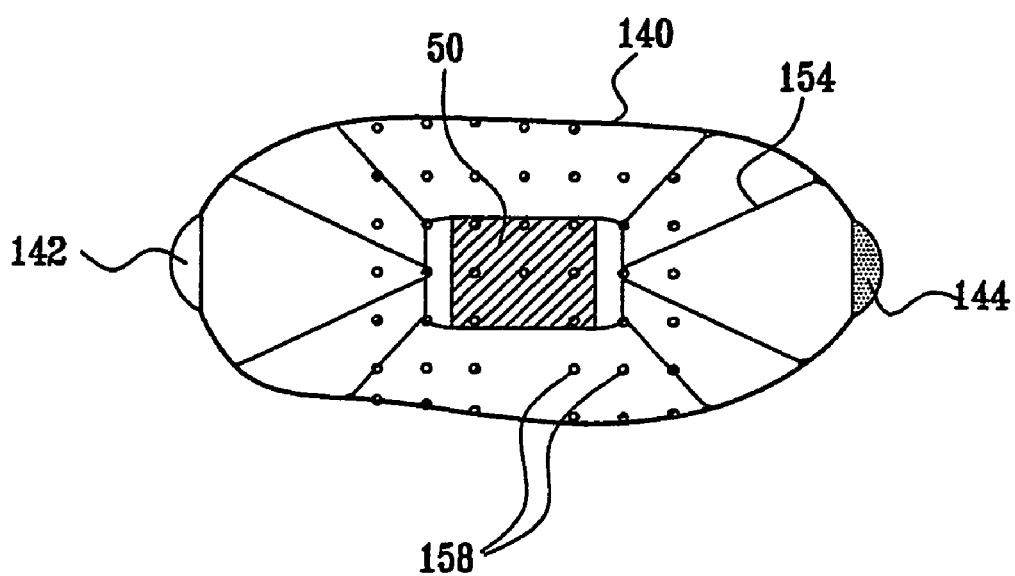
Figure 6C:
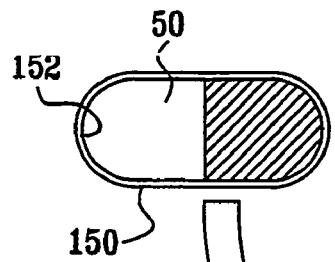
Figure 6C:
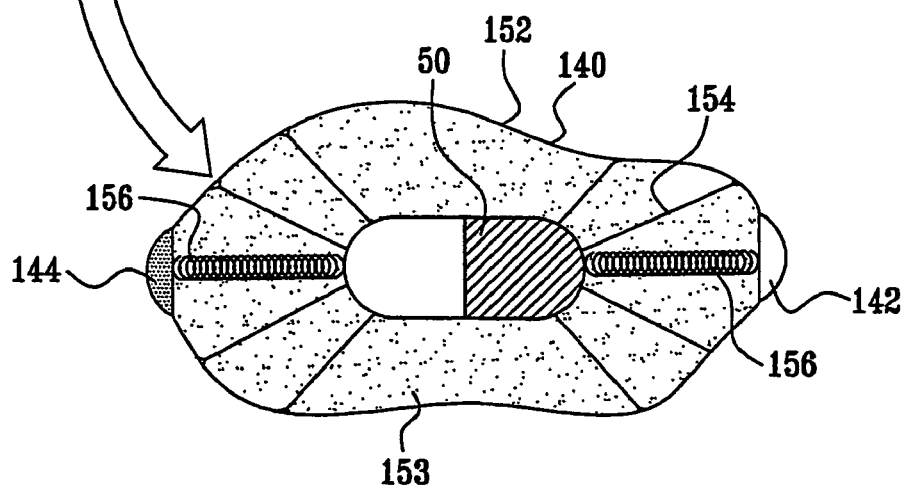
Figure 6D:
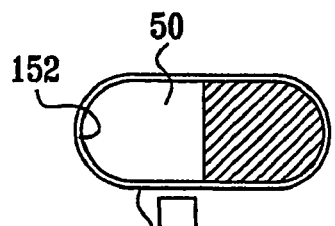
Figure 6D:
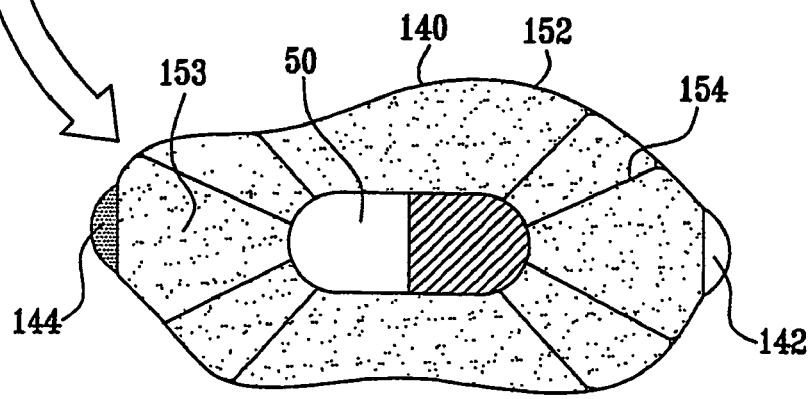

Reference is made to FIGS. 6C and 6D. In an embodiment of the present invention, capsule 50 is coated with a pH-sensitive coating 150 adapted to dissolve at a pH, such as about 7, which is expected at the end of the small intestine and in the colon. Alternatively or additionally, other mechanisms are used to detect the capsule's arrival in the colon, such as mechanisms incorporating polymers that react and dissolve with enzymes released by bacteria in the colon. These bacteria have a marked presence in the colon relative to other parts of the GI tract. For example, a combination of a pH sensitive coating and bacteria dissolving inner coating may be used, such as is sold by Aicello Chemical Co., Ltd. (Aichi, Japan).

Reference is again made to FIGS. 6C and 6D. In an embodiment of the present invention, entrance of capsule 50 into the colon is determined by detecting changes in a pressure wave pattern and/or the presence of XRF due to the contrast agent. These indications may also be used to trigger a mechanical or chemical action to release the outer coating or to enable water from the colon contents to enter the layer under the first coating. In these embodiments, the external surface of balloon 140 comprises a semi-permeable membrane 152 that allows entry into balloon 140 of water and contrast agent. For some applications, balloon 140 contains a layer of a super absorbent hydrogel 153, which expands as water passes through semi-permeable membrane 152. For some applications, capsule 50 is coupled to semi-permeable membrane 152, such as by elongated flexible connecting elements 154, so that capsule 50 remains within balloon 140. For these applications, balloon 140 typically has a length greater than the length of capsule 50, and greater than the width of the colon, such that the capsule will tend to be oriented along the length of the colon. In addition, for some applications, balloon 140 comprises one or more support elements 156 adapted to extend the balloon around the capsule. Elements 156 may, for example, comprise a material such as memory-shaped nitinol (for example, sold by Memory-Metalle GmbH (Weil am Rhein, Germany)).

In an embodiment of the present invention, inflation of balloon 140 beyond the confines of capsule 50 creates a gas-filled medium in which there will be negligible Compton scattering. Thus, Compton backscattering starts on the boundary between balloon 140 and the colon contents, typically a distance of between about 0.5 and about 1.5 cm from the outer surface of capsule 50. In this configuration, in order to measure the total distance from the outer surface of capsule 50 to the wall of the colon, capsule 50 calculates the sum of two separate distances: (a) the distance within the balloon from the capsule to the outer surface of the balloon and (b) the distance from the outer surface of the balloon to the colon wall.

For some applications, the measurement of the distance from the capsule to the outer surface of the balloon is performed using one or more of the following techniques:

Compton backscattering is used to measure changes in the distance from the capsule to the balloon surface, because these changes are reflected in large changes in the total count of backscattered Compton photons. This is due to the fact that within the balloon there is substantially no backscattering. Therefore, changes in the distance of the balloon surface are reflected in changes in backscattering count rates as $1/R^2$, where R is the distance to the balloon surface. The changes in Compton backscattering due to changes beyond the balloon surface are smaller. Optionally, for some applications, these changes are correlated with changes in XRF outside the balloon.

The distance from the capsule to the balloon surface is estimated based on the size of the backscattering projection. This is known because the collimation geometry is known and Compton scattering is substantially negligible in the gas-filled balloon, and thus begins only at the interface between the balloon and the colon contents.

The surface of the balloon is impregnated with point particles 158 of material of high density such as tungsten or tantalum, as shown in FIG. 6B. When particles 158 are illuminated with the gamma and/or X-ray photons from source 60 within capsule 50, some XRF (with a particular spectral line) is detected by radiation detectors 62 on the capsule. The distance to these point sources may be calculated using the count rate for their specific energy window from several detectors, using the following equation:

$$\theta(r, \varphi) = \frac{1}{r^2} * \cos(\varphi) \qquad \text{(Equation 2)}$$

given that the distance depends on the range r and the angle to the point source.

Figure 6E:
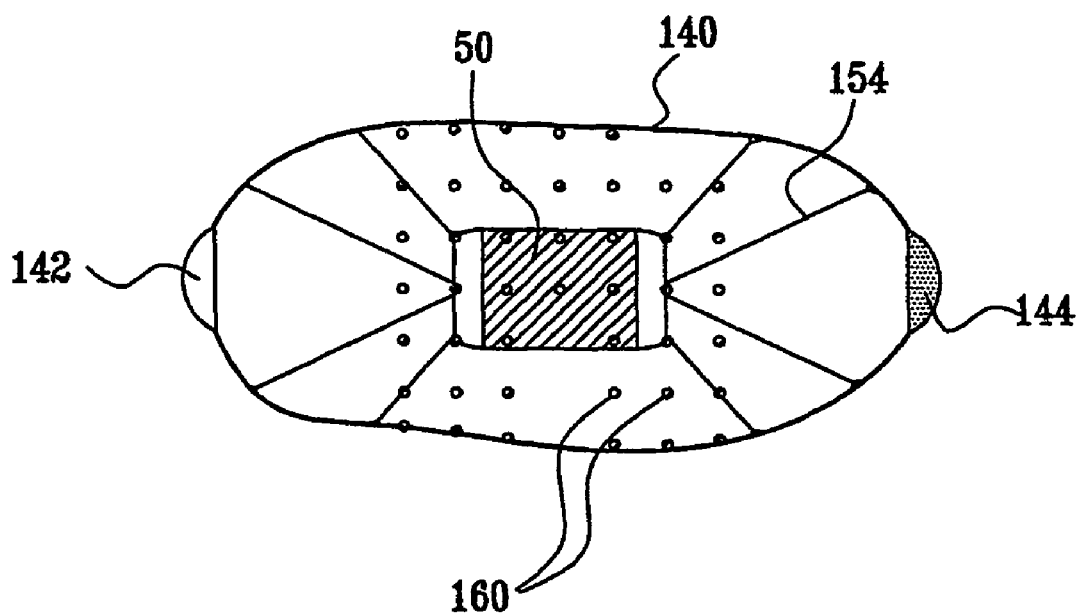

The surface of balloon 140 comprises (e.g., is impregnated with) small gamma and/or X-ray radiation point sources 160, as shown in FIG. 6E. Point sources 160 typically comprises short-lived gamma radiation sources such as T1201, In111, or other materials emitting gamma radiation having one or more energy levels. The distance from the surface of the balloon to these point sources is typically determined using the techniques described immediately above with reference to Equation 2, mutatis mutandis.

In order to estimate the distance from the surface of the balloon to the wall of the colon, the capsule typically analyzes XRF emitted from the contrast agent (or other orally-administered high Z material in the GI tract). The XRF count rate is related to, e.g., proportional to, the volume of colon contents mixed with contrast agent between the colon and the balloon surface.

Reference is again made to FIG. 6E. In an embodiment of the present invention, the surface of balloon 140 comprises radiation point sources 160, as described above. In this embodiment, capsule 50 typically does not comprise radiation source 60. In this embodiment, capsule 50 and/or external data analysis software map: (a) the geometry of the external surface of balloon 140, and (b) anatomical structures of the colon that (i) come in contact with balloon 140 or (ii) are in a vicinity of balloon 140. Typically, balloon 140 comprises fewer than 40 point sources 160, and capsule 50 comprises fewer than 40 radiation detectors 62. The photons emitted from point sources 160 travel in all directions. The photons that travel in the direction of radiation detectors 62 are detected by the detectors at the respective energy windows of the photons. Some of the photons that travel in the direction of the colon contents undergo Compton scattering, such that some photons return to the detectors at about 180 degrees from the incident photons. These scattered photons are registered at the appropriate energy windows by the capsule radiation detectors and associated electronics. Capsule 50 and/or external data analysis software use (a) the knowledge of the positions on the balloon surface of point sources 160 in relation to one another and (b) the detection of the primary and scattered photons by the detector array on the capsule, to map anatomical structures of the colon, whether or not these elements come in contact with the balloon. Typically, the position of each of the sources and the backscattering contribution from each source are determined by solving a linear equation that describes the detection of the source by a plurality of detectors. Solving such an equation is possible because the capsule typically comprises a plurality of detectors and a smaller plurality of point sources.

For some applications, the following algorithm is used to perform this mapping:

Capsule 50 logs photon counts for each primary (i.e., incident) energy window at which point sources 160 generate photons, at each integration time interval.

Capsule 50 logs photon counts for each Compton approximately 180-degree backscattered energy window corresponding to the primary energy windows at which point sources 160 generate photons, at each integration time interval.

For each detector measurement D(Ek)i, the count for each primary energy window Ek is set equal to the sum of photons arriving from all possible "observed" sources, i.e.:

$$D(Ek)i = \sum_j Sij * \theta(r, \varphi) \qquad \text{(Equation 3)}$$

where Sij is the known intensity of the source (or a matrix representing the relations between a plurality of known sources) for a specific energy window, and $\theta(r,\phi)$ is an unknown functional relating to the geometry of the source Sij and the detector measured counts D(Ek)i. For example, the following equation may serve as a representation of $\theta(r,\phi)$:

$$\theta(r, \varphi) = \frac{1}{r^2} * \cos(\varphi) \qquad \text{(Equation 4)}$$

Using matrix format, the linear transformation can be written as follows:

$$D = S\phi \qquad \text{(Equation 5)}$$

The relations between the sources intensities are typically measured and stored in memory of the capsule during the manufacture of the capsule, or at the start of the procedure prior to inflation of the balloon. These relations remain constant throughout the life of the radiolabeled material of point sources 160.

Since the measured matrix D and the source matrix S are known, it is possible to invert S because it is well behaved and invertible, and the values for $\phi$ can thus be calculated:

$$\phi = S^{-1}D \qquad \text{(Equation 6)}$$

where $\phi$ is a weight function whose values are related to, e.g., proportional to, to the spatial geometry of the balloon surface relative to the detector surface, where the governing rule of the weight matrix is the inverse square rule. In other words, the intensity of a radiation source detected from a distance is inversely proportional to the square of the distance between the source and the radiation detector. It can further be shown that in order to solve the position of the point sources, the number of radiation detectors should be at least 3 times the number of point sources.

Other methods for calculating the position of the sources on the balloon and extrapolating the shape of the balloon surface are also within the scope of the present invention.

For some applications, analysis of XRF photons is used to estimate the distance from the balloon surface to the colon wall, either alone or in conjunction with the distance measurement techniques described hereinabove. For some applications, structures other than a balloon are used to effectively produce an effect similar to that of the balloon, e.g., the extension of the radiation sources to an outer boundary close to the colon wall. When such other structures are used, methods for mapping anatomical structures of the colon, such as the algorithms described hereinabove, are appropriately modified to accommodate these other structures.

In an embodiment of the present invention, an algorithm is provided for identifying a polyp, colorectal cancer, or other abnormality from within the colon lumen based on the differences of densities between the abnormality and normal colon tissue. This algorithm also helps detect cancerous tissue or flat polyps that do not bulge out in to the colon lumen (about 5% of polyps in the Western world, and more than 10% of polyps in Japan). Other methods to treat the data set and make use of the correlation between the measurements to improve the signal-to-noise ratio may be used. (The description that follows relates to single backscattering energy, as well as to multiple backscattering energies and relationships (e.g., ratios or differences) between high and low backscattering energies.)

Best results using this algorithm are generally obtained when at least a portion of capsule 50 or balloon 140 is in contact with the wall of the colon or other internal structure, such that there is substantially no contrast agent between one or more radiation detectors 62 and the colon wall or other structure. Capsule 50 typically travels in close contact with the colon wall, because the capsule typically advances in the colon due to peristaltic squeezing by the colon wall.

The algorithm is typically performed upon determination that at least a portion of the swallowable apparatus has come in contact with a portion of the colon wall or other internal structure. For example, this determination may be made by detecting a reduction in XRF photons to substantially zero at the portion of the apparatus in contact, indicating that substantially no contrast agent is present between the apparatus and the colon wall or other structure.

The algorithm analyzes counts of approximately 180-degree Compton backscattered photons generated responsively to incident photons emitted from radiation source 60 and/or point sources 160 on the surface of balloon 140 (FIG. 6E). The algorithm processes counts for adjacent detectors "observing" the same illuminated spot using Principal Component Analysis (PCA), as follows. The following equation is the general matrix equation describing the transformation to principal components based on N measurements from N adjacent pixels:

$$Y = UX \quad \text{(Equation 7)}$$

where X is a matrix of backscattered photon counts (or some relationship, e.g., ratio or difference, between backscattered photons of different energy windows, such as a high energy window divided by a low energy window). Associated with each pixel Y is the matrix of principal components. U is the N×N unitary matrix deduced from the variance-covariance matrix of X, $$C_x = X^T X \quad \text{(Equation 8)}$$

wherein the variables $x_j$, j (j=1 to N), and N are mean centered. The rows of matrix U are the N normalized eigenvectors of $C_{x_x}$. The covariance matrix of the principal components is then $$C^{x^y} = U C_{x_x} U^{T^T} \quad \text{(Equation 9)}$$

and the variables of the principal components (PCs) are the eigenvalues of $C_x$, ordered such that $\lambda_1 > \lambda_2 \ldots > \lambda_N$.

Since U is a unitary transformation, the total data variance is preserved, i.e., $$\sum_{j=1}^{x} \sigma_{x_{ij}}^2 = \sum_{i=1}^{x} \lambda_j \quad \text{(Equation 10)}$$

where $\sigma_x^2$ are the variances of the original variables $X_j$. This redistribution of variance is useful in information recovery. Since the PCs are uncorrelated, and each $Y_j$ has variance less than the previous component, a few PCs would contain a large percentage of the total variance. In other words, it is expected that, for a layer of generally homogeneous tissue such as the colon muscular walls, a large fraction of the total data variance may be described by a single PC. On the other hand, the presence of a polyp and/or cancerous tissue would induce increased variation of the backscattering photon count ratio coming from the colon walls (compared with uniform colon muscle composition). This complex structure of the $C_x$ would result in the presence of two relevant terms (i.e., two PCs), describing a large fraction of the total variance in more than one PC.

In an embodiment of the present invention, in addition to performing the static analysis of data from adjacent detector pixels, as described above, the same mathematical formulation is implemented on successive positions of the capsule as it moves through the colon. The autocorrelation function of the data collected from the different detectors is used to estimate local movements. (This technique is somewhat analogous to using optical analysis techniques to estimate the changing position of an optical computer mouse.)

In an embodiment of the present invention, methods are provided for detecting and discriminating between gas in the colon and anatomical abnormalities, such as polyps. From time to time, gas bubbles form within the colorectal lumen. These bubbles may be mistakenly identified as possible polyps or another anatomical deformation in the colon. In this embodiment, a set of algorithmic tools and supporting hardware is implemented to help distinguish between air bubbles and polyps or other anatomical deformations within the colon. These algorithmic tools include, but are not limited to:

Compton scattering from gas is substantially lower (typically almost non-existent) than that from tissue (both normal and abnormal). Thus, a gas bubble appears as reduced Compton scattering in all the energy windows. Further, the relationship (e.g., ratio or difference) between high and low energies may not change much in the presence of a gas bubble. Therefore, recognition of reduced Compton scattering in all energy windows and smaller changes in the above relationship is an indication of the presence of gas, because the photons pass through less contrast agent In addition to Compton scattered photons, the capsule also is typically adapted to detect X-Ray fluorescence photons emitted by the high Z atoms of the contrast agent. Air and other gases in the colon do not emit XRF, due to the lower Z number and predominately due to lower density. This enables differentiation between gas pockets and polyps based on the ratio between Compton scattered photons and X-ray fluorescence photons.

Upon formation, gas bubbles tend to rise to the uppermost part of the lumen, because of gravity. Therefore, using tilt relative to center of gravity information from the MEMS chip, a determination is made whether a possible bubble has been detected. Using the information on the direction of gravity, it is possible to ascertain where the gas bubble is with respect to any solid angle sectors that may be detecting changes in count rates associated with the gas bubble.

Gas bubbles, when stable, have a flat surface at their bottom. Therefore, they register differently than a polyp or other bulging anatomical abnormalities within the colon.

Gas bubbles, when unstable, travel away from gravitational pull. Therefore, using information from the MEMS chip, a determination is made whether a possible bubble is traveling near the capsule.

In the final part of the colon and in the rectum, gas may form and later be released from the anus. This registers as a gradual decrease in XRF radiation counts and Compton scattering counts over seconds and minutes, followed by a sharp return to a higher value once the gas has been released.

In order to reduce the amount of gas in the colorectal lumen, a gas absorbing material such as a charcoal compound, or a compound found in commercial products intended for absorption of gas in the GI tract, may be mixed with or administered together with the contrast agent For some applications, the presence of a gas bubble is detected using sound waves (e.g., ultrasound). Gas bubbles have a distinctly different acoustic reflective property compared to that of polyps and other anatomical anomalies within the colon lumen.

In an embodiment of the present invention, in which radiation source 60 comprises a radioisotope, the radioisotope emits beta radiation. Such a beta emitter may comprise, for example, P32, S35, or Xe133. The radioisotope material is placed inside a high atomic number metal enclosure such as gold, lead, tungsten or other material of high atomic number. The chosen material typically has an XRF line at a relatively high energy (e.g., tungsten, with XRF at 67 keV). This arrangement generates XRF secondary photon emission as a result of the excitation of the beta electrons.

In an embodiment of the present invention, an energy-saving protocol is used to save battery power when the capsule is traveling in the GI tract before entering the colon. In accordance with such a protocol, one or more of the techniques described hereinabove for detecting that the capsule has reached the colon are used. Once arrival in the colon has been detected, the capsule starts data collection in order to detect polyps within the colon. This data collection typically lasts on average between 24 and 72 hours. In order to minimize radiation exposure from the capsule, the capsule is designed to emit radiation only when it may be about to move. Such imminent motion may be detected, for example, by sensing the changes in pressure of the colon contents; the capsule is activated when a pressure time-dependant gradient passes a certain threshold. Alternatively or additionally, the capsule may be activated if the capsule changes its tilt angle relative to the earth's gravitational pull vector (this may be detected with the MEMS accelerometer chip). A change in this relative tilt above a certain threshold may indicate that the capsule is about to move. Alternatively or additionally, the capsule may use a combination of these criteria for determining when to activate the radiation source.

Alternatively or additionally, for applications in which the capsule comprises balloon 140, as described hereinabove with reference to FIGS. 6A-E, the trigger for activating the detectors may comprise a pressure gauge that measures the gas pressure in the balloon. As the colon walls start to move, pressure builds in the balloon, thereby activating the capsule to switch on the detector channels and other electronic circuits that have been disabled to save energy. After pressure is reduced, the capsule reverts to a quiescent mode of operation, optionally after a delay.

For some applications, the measurement of pressure on the balloon is performed by monitoring Compton backscattering counts from different detectors while the capsule is in its quiescent mode of operation, using high-energy photons that escape from the shield. A change in the readings from these detectors may indicate that the balloon is at a higher pressure, and thus that the capsule should change into a fully active state in anticipation of possible movement.

In an embodiment of the present invention, a specially-prepared diet is given to the subject prior to swallowing the capsule. This diet includes a contrast agent, as described hereinabove, and a mild laxative to soften the bowel contents and facilitate bowel movement, thereby reducing the average transit time of the capsule. A shorter transit time generally allows the use of more energy per unit time in the capsule, and generally enables the use of short-lived radioisotopes for radiation source 60, such as Tc99m (which has a 6-hour half life).

In an embodiment of the present invention, radiation detectors placed on the subject's body are used to track the position of the capsule. Measuring the relative intensity of the detected radiation from a few detectors with known relative positions between them enables tracking of the position of the capsule in real time. The position of the detectors may be tracked by a magnetic location system or another position tracking system known in the art.

In an embodiment of the present invention, the subject is administered an oral agent that has a high Z (i.e., an atomic number of at least 50, typically between 60 and 100) and emits relatively high X-ray fluorescence in response to incident gamma and/or X-ray radiation. Such an agent may comprise, for example, barium sulfate iodine-based compounds or Gadolinium-based compounds, which are routinely used as GI tract contrast agents, or other compounds that emit X-ray fluorescence at relatively high energy (32 keV for barium). This material is generally confined to the GI lumen. The high Z agent fills the volume of the inner colorectal lumen and aids in the detection of polyps and other anatomical deformations by indicating where there are volumes not occupied by the high Z agent.

Except as described hereinbelow, the principles of operation of this embodiment are generally similar to that of embodiments described hereinabove. As in these other embodiments, the capsule emits gamma and/or X-ray radiation to illuminate the vicinity of the capsule. However, unlike in these other embodiments, the purpose of this illumination is to excite the high Z agent to emit X-ray fluorescence (XRF). The X-ray radiation emitted by the XRF process is then detected and processed by the capsule.

Figure 11A:
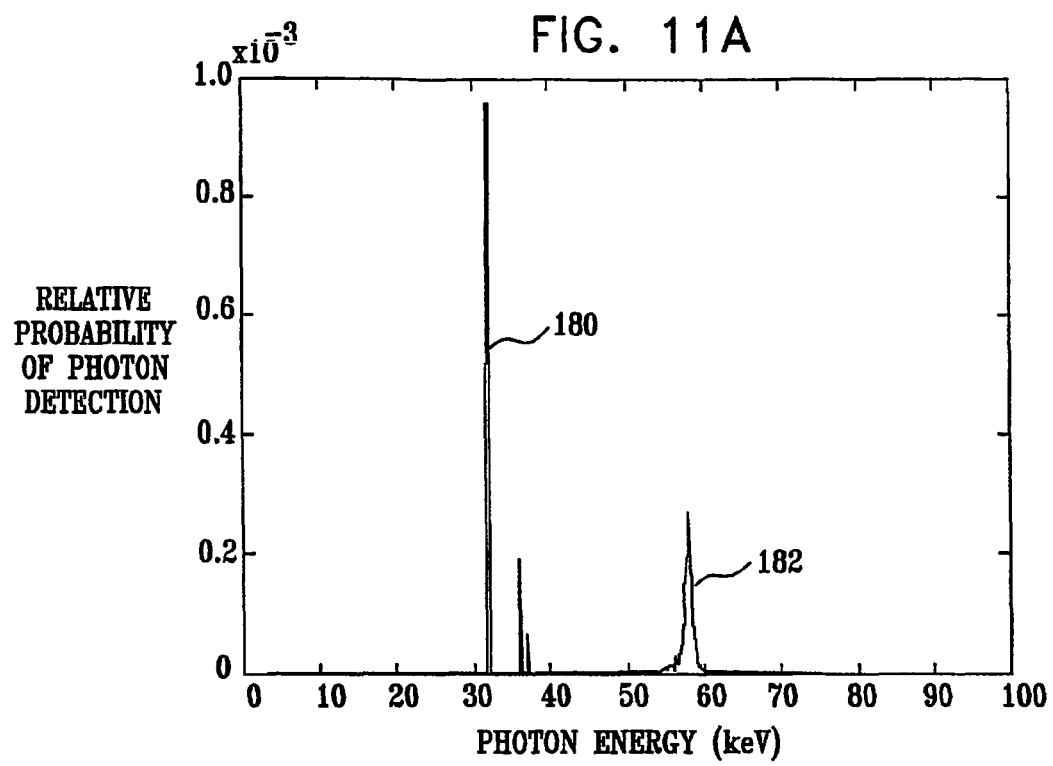
FIGS. 11A-C are graphs showing experimental results measured in accordance with an embodiment of the present invention.
Figure 11B:
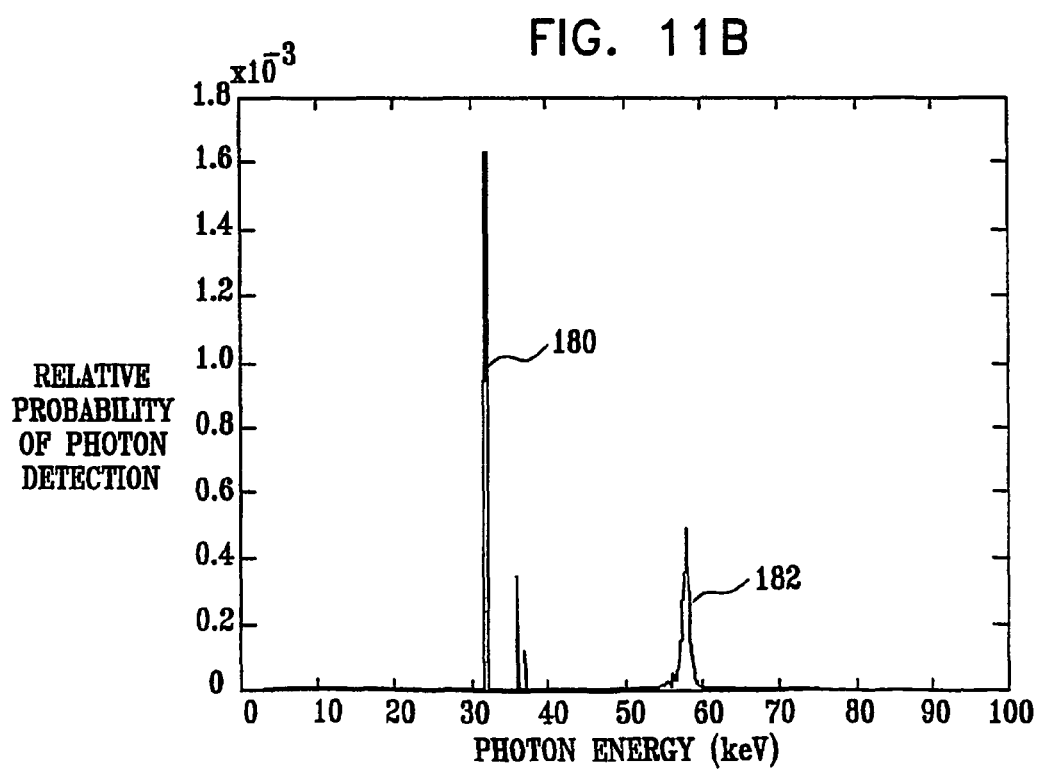
Figure 11C:
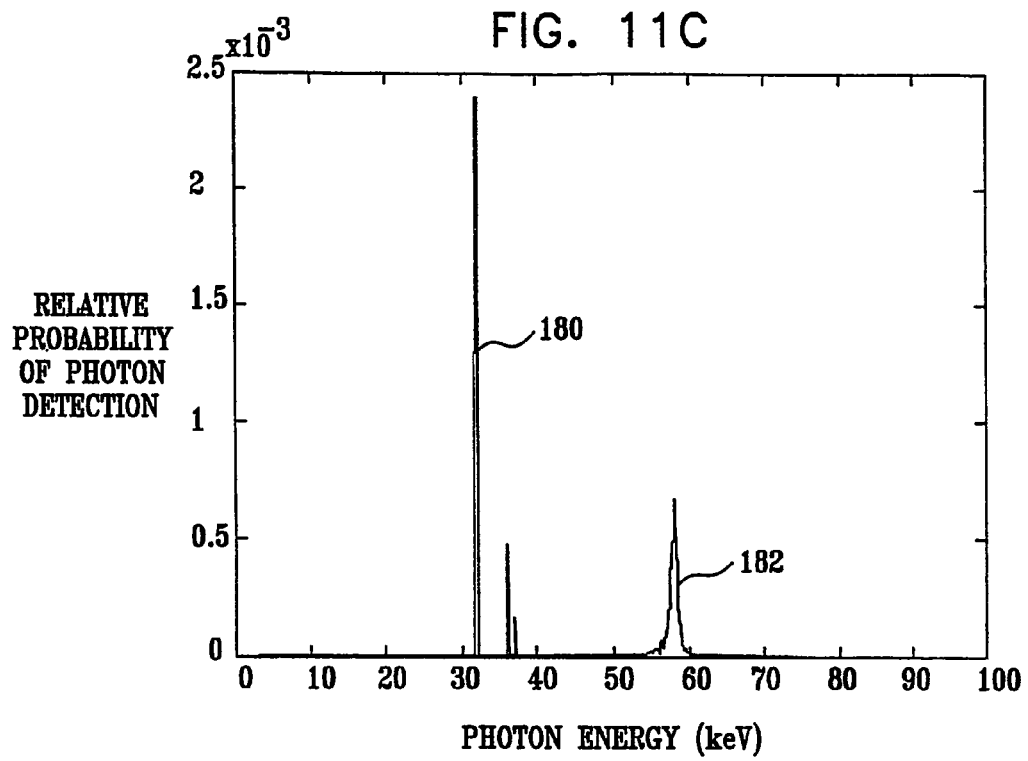

Reference is made to FIGS. 11A-D, which are graphs showing experimental results measured in accordance with an embodiment of the present invention. FIGS. 11A, 11B, and 11C are graphs showing energy spectrums using 2% BaSO4 high Z agent depths of 1 cm, 2 cm, and 3 cm, respectively, in accordance with an embodiment of the present invention.

Figure 11D:
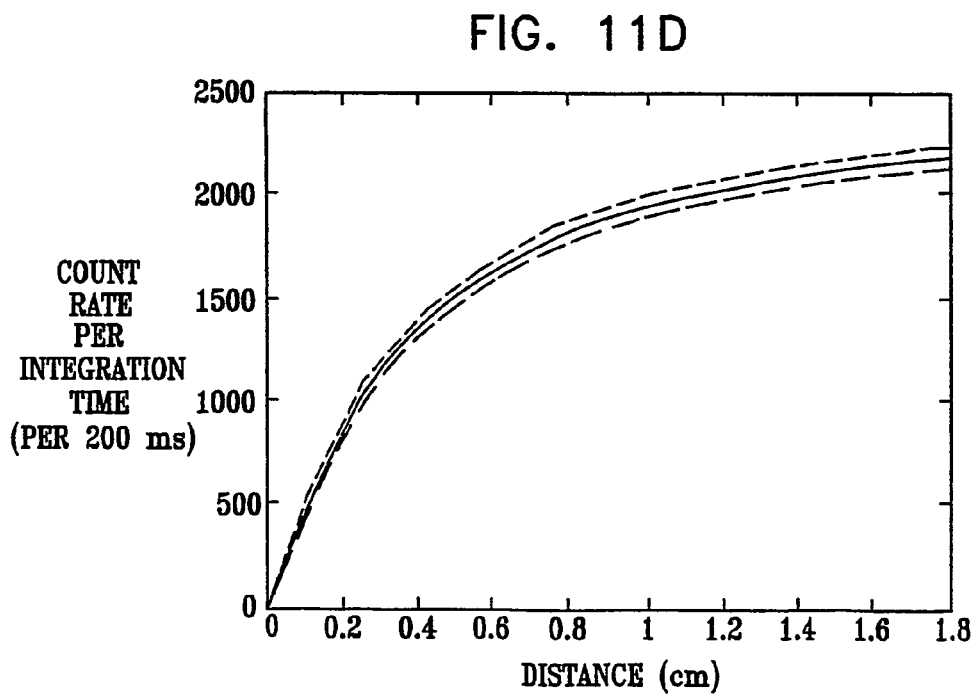
FIG. 11D is a plot of X-ray fluorescence count rates vs. contrast agent depth, in accordance with an embodiment of the present invention.

Each graph shows a BaSO4 XRF spectral line 180 and a Compton backscattering spectral line 182, measured at a backscattering angle of 180 degrees. As can be seen in the graphs, the XRF photon count rate depends on the depth of high Z agent (BaSO4). FIG. 11D is a plot of the integral under the BaSO4 XRF spectral line vs. high Z agent depth, which also illustrates this dependency of photon count rate on depth of high Z agent, in accordance with an embodiment of the present invention. (The solid line shows the mean count rates, and the dashed lines show plus or minus one standard deviation.)

Analysis of the XRF data that are received from the capsule is generally similar to the analysis performed in embodiments described hereinabove. However, XRF photon counts decrease in the presence of a polyp or other anatomical anomaly, while Compton scattering photon counts increase in the presence of a polyp or other anatomical anomaly.

In accordance with an embodiment of the present invention, both Compton scattered photons and XRF photons counts are measured, and the combined information is utilized to identify the presence of a polyp or other anatomical anomaly. In this XRF/Compton embodiment, the two different types of radiation are separately counted, by evaluating different energy windows corresponding to the two separate energies. Typically, the photon energy of the radiation source is selected such that incident photons from the capsule have a sufficiently high energy so that the approximately 180-degree Compton scattered energy is well separated from the XRF of the contrast agent. Use of both XRF and Compton scattered photon counts typically improves the statistics derived from the received photons.

In an embodiment of the present invention, the combination of Compton scattering photons and XRF photons is used to estimate the absolute distance from each of the detectors on the capsule to the colon inner lumen wall. This information is then used (typically retrospectively, when analyzing the data from the capsule) to reconstruct the inner colon wall surface curvatures as a function of time (or as a function of another parameter, such as distance traveled in the colon, typically as determined using information from the MEMS sensors or information based on the autocorrelation function of the count rates from the various detectors).

For some applications, the following absorption equation is used to estimate the distance from the colon wall to the capsule at any given time:

$$I = \phi(C,D) I_0 Exp(-\mu x) \quad \text{(Equation 11)}$$

where:
- I is the photon intensity (for a specific energy window) measured by the detector;
- $\phi(C,D)$ is a function describing the measurement efficiency that depends on collimation geometry and detector efficiency;
- $I_0$ is the photon intensity at the radiation source (for the same specific energy window);
- $\mu$ is the absorption coefficient of the colon contents, which depends on the overall chemical composition and specific density; and
- x is the distance in centimeters.

For some application, a method is provided for estimating the absorption coefficient $\mu$. The following observations will aid in understanding the description of this method hereinbelow:

- The probability of Compton scattering interaction depends on electron density, and is therefore linearly proportional to the density of the colon contents;
- Most photon absorption in the contrast agent (both on the way from the capsule and on the way back to the capsule after Compton scattering) is due to photoelectric interaction, which varies as a function of $Z^5$; and
- The density of the material within the colon is similar to the density of the material outside the colon and generally in the body (as far as Compton scattering interaction probabilities are concerned).

The method for estimating the absorption coefficient $\mu$ of the colon contents (including the contrast agent) typically comprises:

- determining which detectors on the capsule were in contact with the wall of the small intestine at any given time. This determination is typically made by identifying which detectors at any given time were recording a very low level of XRF, as this is an indication that the detectors were in contact with the wall. (XRF is measured at a substantial level in response to the incoming photons passing through the contrast agent. However, photons striking a detector that is in contact with the small intestine wall pass through essentially no contrast agent.) This determination is typically made by analyzing the data recorded in external recording unit 52. An evaluation is made of the mean Compton scattering photon count recorded for each detector when it was in contact with the small intestine wall. This corresponds to x=0 in the absorption equation shown above;
- separating the capsule's detectors from the wall of the colon by at least a known minimum separation distance. The detector which is recording the smallest distance is, therefore, at the known minimum separation distance. For some applications, this separation is achieved using extenders, such as described hereinbelow with reference to FIG. 7A or 7B. This separation is performed when the capsule enters the colon. Entry of the capsule into the colon can be detected using a variety of methods, such as those described hereinabove; and
- calculating the absorption factor $\mu$ of the colon contents including the contrast agent, using Equation 11 and the Compton scattered count rates measured in the first two steps of this method.

Using this calculated value of $\mu$, the time-varying distance from any detector to a near portion of the colon wall is calculated, for that detector's entire period of movement through the colon. In an embodiment, this calculation is based on a model using a semi-log graph, where the count rate is on the y-axis and the distance is on the x-axis. The slope of such a graph is the calculated $\mu$, based on the measurements made in the first two steps of the $\mu$ calculation method.

In an embodiment of the present invention, the subject swallows radiolabeled material that is indigestible and remains only within the confines of the GI tract. Later, the subject swallows a capsule equipped with gamma radiation sensors that is in communication with an external recording unit that is worn by the subject. Except as described herein, the principles of operation of this embodiment are generally similar to that of embodiments described hereinabove.

Figure 3:
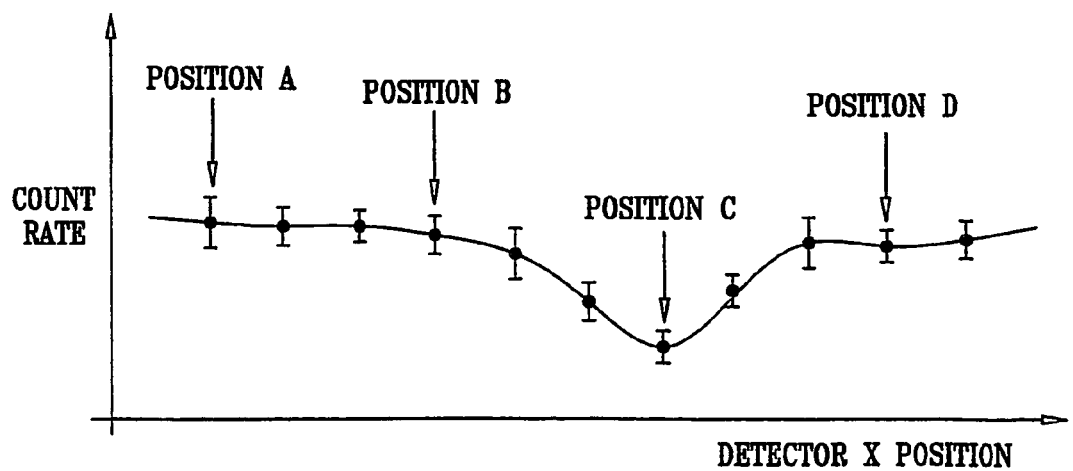
FIG. 3 is a graph showing exemplary experiment results of an experiment similar to that of FIGS. 2A-E, in accordance with an embodiment of the present invention.

This embodiment of the invention is based on the following physical principles, which are described with reference to FIG. 3, which is a graph showing exemplary experiment results of an experiment similar to that described hereinabove with reference to FIGS. 2A-E, in accordance with an embodiment of the present invention. A container similar to container 12 of FIGS. 2A-D is filled with radiolabeled liquid or low viscosity gel, and a small water-filled balloon, similar to balloon 18 of FIGS. 2A-D, is placed at the bottom of the container. A collimated radiation detector similar to detector 16 of FIGS. 2A-D is passed above the container, maintaining a constant distance from the bottom of the container (no radiation source similar to source 14 of FIGS. 2A-D is used in this experiment). At a plurality of points along the path of the detector, gamma or X-ray radiation counts per second are logged. As the detector passes above the position of the water balloon (position C), the count rate reading declines, as shown in FIG. 3. Two physical principles combine to produce this effect:

because the media is liquid or low viscosity gel, the concentration of radioactive material is evenly distributed within this media, assuming that sufficient time has passed after the introduction of the radioisotope; and the number of photons detected per unit time is directly proportional to the volume that the collimated detector is "observing." In other words, the probability of detecting a photon originating from an isotope that decays into more stable nuclei is directly proportional to the volume of radioactive nuclei that is "observed" by the collimated detector.

The principles of operation of this embodiment are generally similar to that of embodiments described hereinabove, except that the high-energy photons of this embodiment are emitted from the radiolabeled material swallowed by the subject, rather than from the capsule (or the point sources of the balloon). The radiolabeled material is typically similar to that used routinely for the study of colon transit times. For example, the radiolabeled material may be an orally administered tracer such as I-131-cellulose, cation-exchange resin particles (0.5-1.8 mm diameter) labeled with In111 in a gelatin capsule, Ga67-citrate, or other such materials which are administrated orally and remain within the confines of the GI tract. (See, for example, the above-mentioned article by Camilleri et al.)

The capsule of this embodiment is similar to capsule 50, such as described hereinabove with reference to FIG. 4. However, unlike capsule 50, the capsule of this embodiment typically does not comprise any radiation source. Furthermore, the radiation detectors of the capsule of this embodiment typically are collimated. The radiation detectors are typically arranged in a sphere, such that they "observe" the entire 4 pi squared sphere (or a portion of it) surrounding the capsule. The collimation of the detectors enables each of the detectors to "observe" a confined (relative to the sphere) solid sector.

The capsule travels through the GI tract and measures the photons that hit its radiation detectors. This measurement is typically performed generally constantly, unless the capsule is in a power-saving mode. The count rate information received from each of the radiation detectors is stored together with the time stamp for each measurement. Within this unit integration time, it is assumed that the capsule and its surrounding colon wall and the radio labeled material are in quasi-steady state. Taking small enough time intervals and integrating the counts over these small periods allow for this quasi-steady state assumption. These data are stored in the capsule and typically sent by the capsule to the external recording unit from time to time.

Analysis of the data from the capsule is substantially similar to the analysis described hereinabove. The presence of a protruding anatomical structure reduces the gamma count rate received from that area since the structure displaces radiolabeled colon contents, resulting in a lower count reading.

Figure 7A:
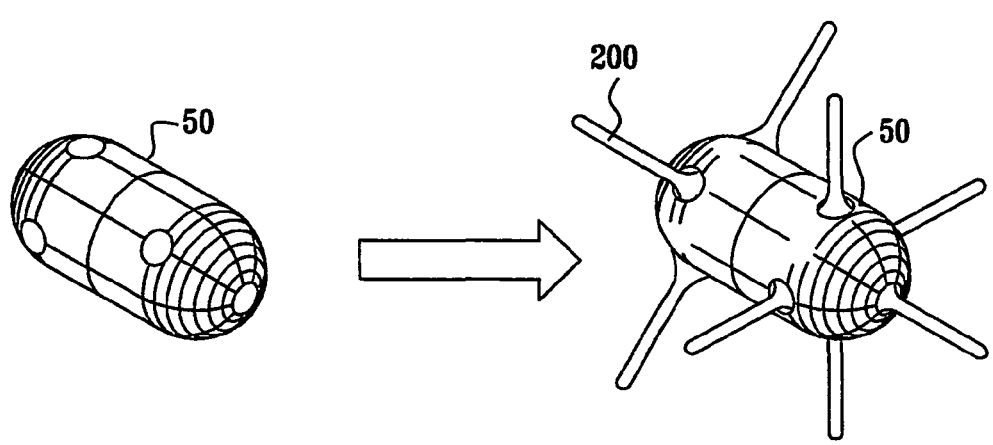
FIGS. 7A and 7B are schematic illustrations of extending elements, in accordance with embodiments of the present invention.
Figure 7B:
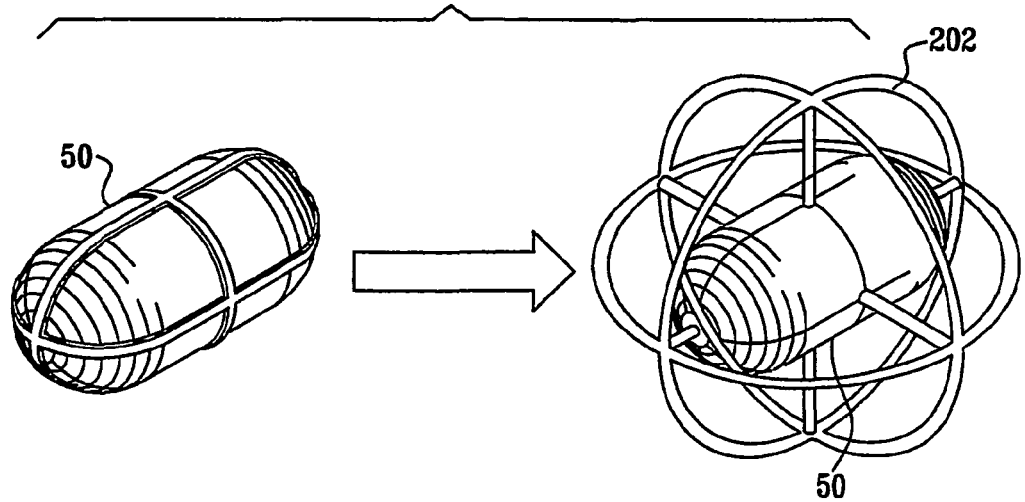

Reference is now made to FIGS. 7A and 7B, which are schematic illustrations of extending elements, in accordance with embodiments of the present invention. These extending elements are deployed when capsule 50 reaches an area of diagnostic interest in the GI tract, typically the colon. In their expanded positions, the extending elements maintain capsule 50 a small distance from the wall of the colon. For some applications, capsule 50 comprises a material that reacts based on a chemical trigger, such as a change in pH, when the capsule reaches the vicinity of the colon (for example, using techniques described in the above-mentioned article by Camilleri et al.). The chemical reaction causes the deployment of the extending elements. Alternatively or additionally, materials are utilized that expand when GI tract liquids are absorbed therein, thereby deploying the extending elements.

For some applications, the expander elements comprise an elastic, flexible material. The elasticity and flexibility of expander elements are such that even if the elements unintentionally fully deploy in the small intestine, they are sufficiently flexible not to interfere with the normal progression of the capsule in the small intestine. Such extenders may comprise a material such as a hydrogel. This type of material typically absorbs 50 times its weight. Typically, the absorbing material is enclosed in a fabric that allows water to enter but prevents the gel from escaping.

For some applications, the extending elements comprise legs 200, as shown in FIG. 7A. Alternatively, the extending elements comprise an expandable ring structure 202, as shown in FIG. 7B. The rings of structure 202 are initially held tightly packed around capsule 50 by a dissolving material, such as a pH-sensitive material that dissolves at a pH specific to the colon. When the dissolving material dissolves in the colon, the rings are released and expand around the capsule. Further alternatively, the extending elements comprise another expanding geometrical form.

Figure 8A:
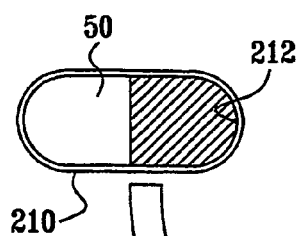
FIGS. 8A-C are schematic illustrations of additional extending elements, in accordance with embodiments of the present invention.
Figure 8A:
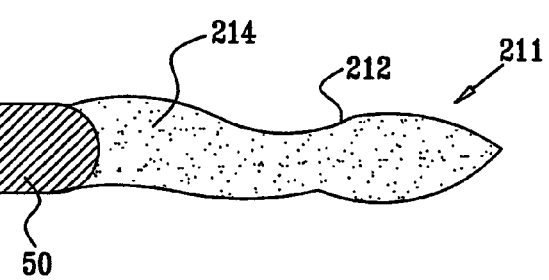
Figure 8B:
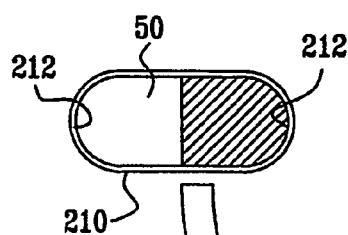
Figure 8B:
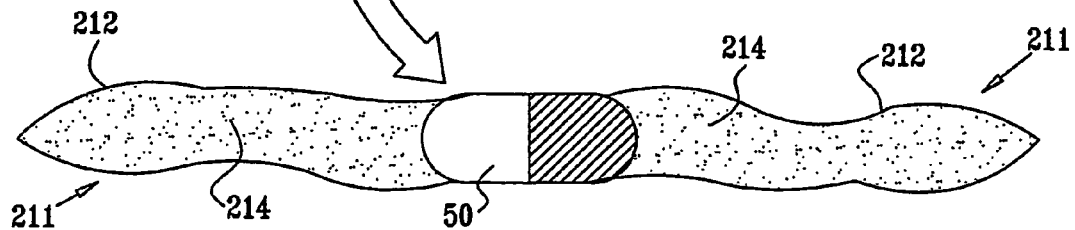

Reference is made to FIGS. 8A and 8B, which are schematic illustrations of additional extending elements, in accordance with embodiments of the present invention. In these embodiments, capsule 50 typically comprises one or two expandable flexible chambers 211, coupled to one end of capsule 50 (FIG. 8A) or both ends of the capsule (FIG. 8B). Each chambers 211 comprises a semi-permeable expandable membrane 212, which surrounds a super-absorbent hydrogel 214. Capsule 50 is typically coated with a coating 210 that is pH-sensitive to the pH of the colon, and/or sensitive to bacterial enzymes found in the colon. When capsule 50 reaches the colon, coating 210 dissolves, allowing liquids of the colon (such as water and possibly contrast agent) to pass through membranes 212, and be absorbed by hydrogel 214. This absorption by hydrogel 214 expands chambers 211, such that capsule 50 together with the chambers has a length greater than the width of the lumen of the colon, thereby forcing the long axis of capsule 50 to be oriented parallel to the longitudinal axis of the colon lumen. The expansion of chambers 211 also generally minimizes movement of the capsule when there is no mass movement of the colon contents. Even if chambers 211 unintentionally fully deploy in the small intestine, the chambers will not obstruct the movement of the capsule within the small intestine.

Figure 8C:
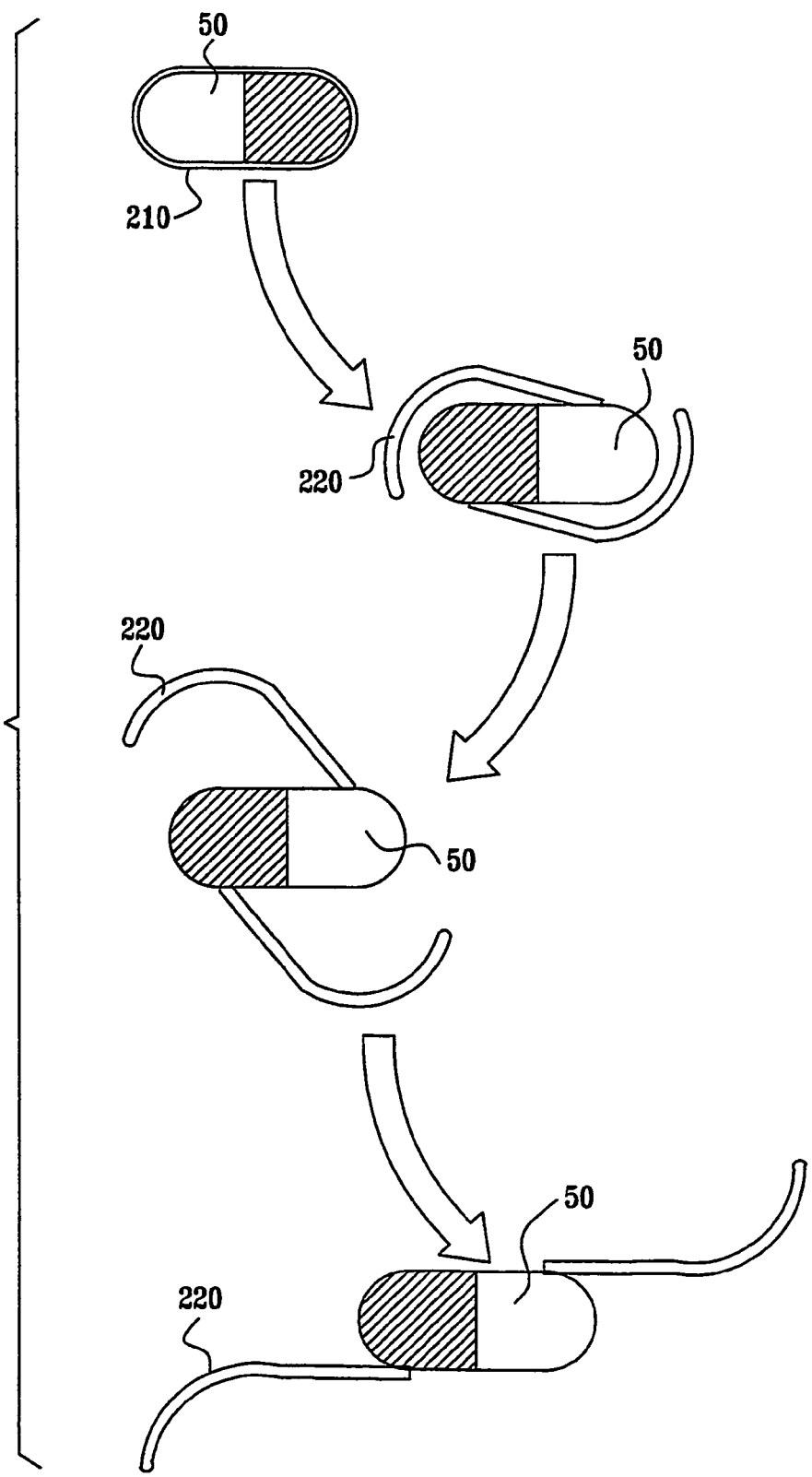

Reference is made to FIG. 8C, which is a schematic illustration of yet another extending mechanism, in accordance with an embodiment of the present invention. In this embodiment, the extending elements comprise unfolding elements 220. Unfolding elements 220 typically comprise a flexible material that extends when coating 210 dissolves. Other forms and shapes for the extending elements will be apparent to those skilled in the art who have read the present application, and are within the scope of the present invention.

For some applications, other chemical or non-chemical techniques are used for triggering the deployment of the various extending mechanisms described herein. For example, capsule 50 may receive a signal from a site external to the subject, or may detect electrical signals characteristic of the colon, and responsively thereto may mechanically, electrically, chemically, or otherwise deploy the extending elements.

In an embodiment of the present invention, a contrast agent, or radiolabeled agent, and/or high Z agent is encapsulated in capsule 50 or in a separate agent storage capsule that dissolves when the ambient pH becomes characteristic of a desired portion of the GI tract. In response, the agent is released near or in the colon, improving the effective concentration of the agent in the colon.

In an embodiment of the present invention, capsule 50 is tracked by a navigation system that adds position information to the capsule data. Such a navigation system may comprise, for example, a set of radio receivers that track the capsule by measuring, at different positions on the subject's body, the relative amplitudes of RF signals transmitted by the capsule. Other embodiments utilize ultrasound-based localization, wherein the capsule serves as a transponder to signals coming from a few locations on the subject's body, and time-of-flight measurements provide position location. Other position-location technologies known in the art, such as magnetic-field based location sensing, are used for some applications.

In an embodiment of the present invention, capsule 50 comprises electrically-conductive electrodes coupled to its surface, and a pulse generator in the capsule that is controlled by the capsule's microcontroller. In this embodiment, the capsule is adapted to stimulate the colon electrically, thereby inducing a controlled mass movement. Such stimulation techniques are described, for example, in U.S. Pat. No. 6,453,199 to Kobozev, which is incorporated herein by reference, and RU No. 936931 MKI A61 N 1/36 BIR 1982, which is incorporated herein by reference. The capsule typically repeatedly performs the following steps: (a) awakens from a quiescent mode and begins to acquire data, (b) stimulates the colon to effect mass movement, and (c) upon the cessation of mass movement, ceases to acquire data and reenters the quiescent mode. In this manner, the capsule can be controlled and data acquired at relevant times. The subject may also be informed that the capsule has started its imaging within the colon. Alternatively, the subject may choose when to start such process. In such a case, the entire screening of the colon may have a short duration. In this case, the stool may be soft and the subject may elect to use a toilet during the few minutes required to complete the screening of the colon and rectum.

In an embodiment of the present invention, colon muscles are observed during a contraction, using the observation and analysis techniques described herein. Healthy colon muscles contract in a generally cylindrically symmetrical fashion. The potential presence of an anatomical anomaly is detected by observing a deviation from such cylindrical symmetry. Such an anomaly may be a polyp or other anatomical anomaly that may harbor cancerous or pre-cancerous tumors. Deviations along the path of the colon from one area to another may also indicate the presence of an anatomical abnormality.

In an embodiment of the present invention, the capsule's power source comprises a "nuclear battery," utilizing the radioactive material in the capsule as a beta emitter. For example, techniques and apparatus may be used that are described in U.S. Pat. No. 5,721,462 to Shanks, which is incorporated herein by reference.

For some applications, techniques and apparatus described in the above-mentioned U.S. Provisional Patent Application 60/531,690 and/or 60/559,695 are applied in combination with the techniques and apparatus described herein.

It is noted that whereas some embodiments of the present invention are described herein with respect to causing the subject to swallow a contrast agent such as barium (which increases absorption of photons, and thus provides a way to differentiate between the wall of the GI tract and the contents of the lumen), in other embodiments of the present invention the subject instead swallows a contrast agent which has reduced absorption relative to the wall of the GI tract. For example, nutritional fibers have lower absorption than the absorption of the GI tract wall and tissue outside of the GI tract, and, therefore, when the capsule passes by a polyp or other abnormality, the recorded Compton scattered photons will decrease. As used herein, including in the claims, "contrast agent" includes both positive-attenuation and negative-attenuation contrast agents.

Although in some embodiments of the present invention capsule 50 and/or data-recording unit 52 are described as performing certain calculations and/or analyses, all or a portion of these calculations and/or analyses may be performed instead by external data analysis software and/or hardware. Similarly, for some applications, calculations and/or analyses described herein as being performed by external data analysis software and/or hardware may be performed by capsule 50 and/or data-recording unit 52.

Although some embodiments of the present invention are described with respect to inspecting the colon of a subject, some of the techniques described herein may also be applicable to other portions of the GI tract, and/or to other body lumens, such as blood vessels, mutatis mutandis.

For simplicity, some embodiments of the present invention are described herein with respect to a scattering angle of 180 degrees, but typically include a range around 180 degrees, as well. For example, the range may be 180 degrees +/− a range parameter, where the range parameter is typically less than 10, 20, or 30 degrees.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for detecting a clinically-relevant feature of a gastrointestinal (GI) tract of a subject, comprising:
   an oral contrast agent consisting essentially of a stable and non-radioactive isotope, adapted to be administered to the subject;
   a capsule adapted to be swallowed by the subject, said capsule including:
   at least one radiation source emitting X-ray or gamma radiation having an energy of at least 10 keV;
   at least one radiation detector comprising at least one collimator configured to detect in a first energy window collimated X-ray fluorescence radiation from the X-ray contrast agent composition excited by the emitted radiation, and to detect in a second energy window Compton-backscattered radiation from the X-ray contrast agent and the wall of the GI tract produced in response to the emitted radiation; and
   a control unit configured to analyze data regarding the detected X-ray fluorescence radiation and Compton-backscattered radiation to identify a distance between the capsule and a wall of the GI tract,
   said control unit further configured to compute a ratio between the Compton-backscattered radiation and the X-ray fluorescence radiation signals for distinguishing between gas in the GI tract and the clinically-relevant feature.

2. The apparatus according to claim 1, wherein the contrast agent composition comprises an agent having a high Z adapted to be swallowed by the subject.

3. The apparatus according to claim 1, wherein the radiation source comprises a radioisotope.

4. The apparatus according to claim 1, wherein the radiation source comprises at least one collimator which collimates the radiation emitted by the radiation source.

5. The apparatus according to claim 1, wherein the clinically-relevant feature includes an estimate of a distance from a site of the capsule to a wall of the GI tract.

6. The apparatus according to claim 5, wherein the distance is estimated from an intensity measurement of the Compton backscattered radiation.

7. The apparatus according to claim 5, wherein the distance is estimated from an intensity measurement of the X-ray fluorescence (XRF) radiation generated responsive to the emitted radiation.

8. The apparatus according to claim 1, wherein the radiation source emits the radiation from the capsule only during a portion of a time that the capsule is in the GI tract.

9. The apparatus according to claim 8, wherein the capsule comprises a sensor, adapted to sense a parameter indicative of possible imminent motion of the capsule in the GI tract, and wherein the radiation source emits the radiation in response to sensing the parameter by the sensor.

10. The apparatus according to claim 1, wherein the capsule comprises an inflatable balloon, adapted to inflate around the capsule.

11. The apparatus according to claim 1, wherein the at least one radiation detector comprises a plurality of radiation detectors, arranged to detect radiation arriving from a plurality of respective detection directions.

12. The apparatus according claim 1, wherein the capsule comprises at least one radiation shield.

13. The apparatus according to claim 12, wherein the capsule comprises an actuator adapted to move at least one of the radiation source and the shield, such that the radiation shield does not block the radiation emitted from the radiation source during the portion of the time.

14. The apparatus according to claim 12, wherein the at least one radiation shield is configured to prevent radiation from being emitted from the radiation source in directions other than a single confined solid sector relative to a sphere surrounding the capsule.

15. The apparatus according to claim 1, wherein the clinically relevant feature includes a pathological abnormality of the GI tract.

16. The apparatus according to claim 15, wherein the pathological abnormality includes a polyp.

17. The apparatus according to claim 1, wherein the control unit is adapted to detect that the capsule has reached an area of clinical interest within the GI tract.

18. The apparatus according to claim 1, wherein the control unit includes means for activating the radiation detector and electronic circuitry upon movement of the colon wall.

19. The apparatus according to claim 17, wherein the capsule comprises a pressure sensor, and wherein the control unit detects that the capsule has reached the area responsively to a change in pressure detected by the pressure sensor.

20. The apparatus according to claim 1, wherein the capsule comprises at least one extending element, which, when extended, maintains the capsule at least a certain distance from a wall of the GI tract.

21. The apparatus according to claim 1, wherein the capsule comprises at least one extending element, which, when extended, orients a long axis of the capsule generally parallel to a longitudinal axis of the GI tract.

22. The apparatus according to claim 21, wherein the extending element comprises an expandable flexible chamber, wherein the flexible chamber comprises a super-absorbent hydrogel, and wherein the flexible chamber expands when the hydrogel absorbs liquids from the GI tract.

23. The apparatus according to claim 1, wherein X-ray contrast agent composition comprises a composition selected from a barium sulfate-based compound, an iodine-based compound, and a gadolinium-based compound.

24. The apparatus according to claim 1, wherein X-ray contrast agent composition comprises a composition selected from Tantalum, Gadolinium, Thorium, Bismuth, and compounds thereof.

25. The apparatus according to claim 14, wherein the at least one radiation detector is arranged for detection of Compton-backscattered radiation at an angle of 180°±30° relative to the angle defined by the solid sector.

26. A method for detecting clinically-relevant features of a gastrointestinal (GI) tract of a subject, comprising:
   orally administering to a subject a radiopaque X-ray contrast agent composition consisting essentially of a stable, non-radioactive isotope;
   orally administering to a subject a capsule emitting X-ray or gamma radiation having an energy of at least 10 keV;
   measuring, from within the GI tract, concurrently in a first energy window a first radiation signal generated responsively to the emitted X-ray or gamma radiation, said measured first radiation signal representing collimated Compton-backscattered radiation, and in a second energy window a second radiation signal representing X-ray fluorescence (XRF) radiation from the X-ray contrast agent;
   computing a ratio between the first radiation signal and the second radiation signal for distinguishing between gas in the GI tract and a clinically-relevant feature.

27. The method of claim 26, wherein the clinically-relevant feature of the GI tract comprises a polyp or another comparable anatomical abnormality, further comprising identifying the polyp or anatomical abnormality from a decrease in the second radiation signal from the XRF radiation accompanied by an increase in the first radiation signal from the Compton-backscattered radiation.

28. The method of claim 26, further computing a ratio between the measured first radiation signal from Compton-scattered radiation and the measured second radiation signal from XRF radiation, and differentiating between gas pockets and polyps based on the computed ratio.

29. A capsule, adapted to be swallowed by a subject, for detecting clinically-relevant features of a gastrointestinal (GI) tract of a subject, comprising:
   at least one radiation source emitting X-ray or gamma radiation having an energy of at least 10 keV;
   at least one radiation detector comprising at least one collimator configured to detect a first energy window collimated X-ray fluorescence radiation from the X-ray contrast agent composition excited by the emitted radiation, and to detect a second energy window Compton-backscattered radiation from the X-ray contrast agent and the wall of the GI tract produced in response to the emitted radiation; and
   a control unit configured to compute a ratio between the Compton-backscattered radiation and the X-ray fluorescence radiation signals for distinguishing between gas in the GI tract and a clinically-relevant feature.

* * * * *